(12) United States Patent
Markussen et al.

(10) Patent No.: US 7,229,964 B2
(45) Date of Patent: *Jun. 12, 2007

(54) INSULIN DERIVATIVES

(75) Inventors: Jan Markussen, Herlev (DK); Ib Jonassen, Valby (DK); Svend Havelund, Bagsvaerd (DK); Jakob Brandt, Bronshoj (DK); Peter Kurtzhals, Brookline, MA (US); Per Hertz Hansen, Lyngby (DK); Niels Christian Kaarsholm, Vanlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 544 days.

This patent is subject to a terminal disclaimer.

(21) Appl. No.: 10/620,651

(22) Filed: Jul. 16, 2003

(65) Prior Publication Data

US 2004/0067874 A1   Apr. 8, 2004

Related U.S. Application Data

(60) Continuation of application No. 09/861,687, filed on May 21, 2001, now Pat. No. 6,620,780, which is a division of application No. 08/932,082, filed on Sep. 17, 1997, now Pat. No. 6,251,856, which is a continuation of application No. PCT/DK96/00107, filed on Mar. 18, 1996, which is a continuation-in-part of application No. 08/448,210, filed on May 23, 1995, now abandoned.

(30) Foreign Application Priority Data

Mar. 17, 1995   (DK) .................................. 0276/95

(51) Int. Cl.
*A61K 38/28*   (2006.01)
(52) U.S. Cl. ........................ 514/3; 514/866; 530/303
(58) Field of Classification Search ............... None
See application file for complete search history.

(56) References Cited

U.S. PATENT DOCUMENTS

| | | | |
|---|---|---|---|
| 3,528,960 A | 9/1970 | Hass et al. | |
| 3,869,437 A | 3/1975 | Lindsay et al. | |
| 5,359,030 A | 10/1994 | Ekwuribe | |
| 5,506,202 A | 4/1996 | Vertesy et al. | ............ 514/530 |

FOREIGN PATENT DOCUMENTS

| | | |
|---|---|---|
| EP | 0376156 | 7/1990 |
| EP | 0 511 600 A2 | 11/1992 |
| EP | 0 712861 | 5/1996 |
| EP | 0 712862 | 5/1996 |
| GB | 1 492 997 | 11/1977 |
| JP | 57-67548 | 4/1982 |
| WO | WO 91/12817 | 9/1991 |
| WO | WO 92/00321 | 1/1992 |
| WO | WO 92/01476 | 2/1992 |
| WO | WO 95/07931 | 3/1995 |

OTHER PUBLICATIONS

Hashimoto et al., Pharm. Res. 6 : 171-176, 1989.*
Kodama et al., Abstract of Japan, vol. 14, No. 7 (C-673), (1988).
Muranishi et al., Abstract of Japan, Hei 1-254699 (Oct. 11, 1989).
Samuel et al., (1978) Clin. Exp. Immunol. 33:252-260.
Kurtz et al., (1983) Diabetologia 25:322-324.
Markussen et al. Prot. Engineer. 2(2) :157-166, 1988.
Markussen et al. Prot. Engineer. 1(3) :205-213, 1987.
Harmann et al. Diabetes Res. Clin. Prac. 16: 175-181, 1992.

* cited by examiner

*Primary Examiner*—Gary Nickol
*Assistant Examiner*—Gyan Chandra
(74) *Attorney, Agent, or Firm*—Richard W. Bork

(57) ABSTRACT

The present invention relates to insulin derivatives in which a lipophilic group having from 12 to 40 carbon atoms is attached to the α-amino group of the N-terminal amino acid in the B-chain or to the carboxy group of the C-terminal amino acid in the B-chain have a protracted profile of action.

13 Claims, 3 Drawing Sheets

```
            #94 ↓
    5'-TAAATCTATAACTACAAAAAACACATA-3' EcoRI
    5'-CTTAAATCTATAACTACAAAAAACACATACAGGAATTCCATTCAAGAATAGTTCAAACAA
907 ---+---------+---------+---------+---------+---------+------ 966
    3'-GAATTTAGATATTGATGTTTTTTGTGTATGTCCTTAAGGTAAGTTCTTATCAAGTTTGTT

GAAGATTACAAACTATCAATTTCATACACAATATAAACGATTAAAAGAATGAGATTTCCT
967 ---+---------+---------+---------+---------+---------+------ 1026
    CTTCTAATGTTTGATAGTTAAAGTATGTGTTATATTTGCTAATTTTCTTACTCTAAAGGA
                                                       MetArgPhePro   4

TCTATTTTTACTGCTGTTTTATTCGCTGCTTCCTCCGCTTTAGCTGCTCCAGTCAACACT
1027 ---+---------+---------+---------+---------+---------+------ 1086
     AGATAAAAATGACGACAAAATAAGCGACGAAGGAGGCGAAATCGACGAGGTCAGTTGTGA
     SerIlePheThrAlaValLeuPheAlaAlaSerSerAlaLeuAlaAlaProValAsnThr   24

ACCACTGAAGATGAAACGGCTCAAATTCCAGCTGAAGCTGTCATCGGTTACTCTGATTTA
1087 ---+---------+---------+---------+---------+---------+------ 1146
     TGGTGACTTCTACTTTGCCGAGTTTAAGGTCGACTTCGACAGTAGCCAATGAGACTAAAT
     ThrThrGluAspGluThrAlaGlnIleProAlaGluAlaValIleGlyTyrSerAspLeu   44

GAAGGTGATTTCGATGTTGCTGTTTTGCCATTTTCCAACTCCACCAATAACGGTTTATTG
1147 ---+---------+---------+---------+---------+---------+------ 1206
     CTTCCACTAAAGCTACAACGACAAAACGGTAAAAGGTTGAGGTGGTTATTGCCAAATAAC
     GluGlyAspPheAspValAlaValLeuProPheSerAsnSerThrAsnAsnGlyLeuLeu   64

TTTATCAATACTACTATTGCCTCCATTGCTGCTAAAGAAGAAGGTGTTTCTTTGGATAAA
1207 ---+---------+---------+---------+---------+---------+------ 1266
     AAATAGTTATGATGATAACGGAGGTAACGACGATTTCTTCTTCCACAAAGAAACCTATTT
     PheIleAsnThrThrIleAlaSerIleAlaAlaLysGluGluGlyValSerLeuAspLys   84
                                                  3'-CCACAAAGAAACCTATTT

HindIII
                                  5'-TTGGTTGAAGCTTTGTACTTGGTTTGC
     AGATTCGTTAACCAACACTTGTGCGGTTCCCACTTGGTTGAAGCTTTGTACTTGGTTTGC
1267 ---+---------+---------+---------+---------+---------+------ 1326
     TCTAAGCAATTGGTTGTGAACACGCCAAGGGTGAACCAACTTCGAAACATGAACCAAACG
     ArgPheValAsnGlnHisLeuCysGlySerHisLeuValGluAlaLeuTyrLeuValCys  104
     TCT   GCAATTGGTTGTGAACACGCCAAGGGTGAACCAACTTCGAAACATGAACC-5'
       C  A                    #593 ↑
       T    ATGTAGCCTTTGGT
       T              T         TGACGATGCT
     CTTCGACTTCGACTTCGAC        C            A
          .           #3075 ↑   T            G
     GGTGAAAGAGGTTTCTTCTACACTCCTAAG          AGGTATTG-3'
     GGTGAAAGAGGTTTCTTCTACACTCCTAAGGCTGCTAAGGGTATTGTCGAACAATGCTGT
1327 ---+---------+---------+---------+---------+---------+------ 1386
     CCACTTTCTCCAAAGAAGATGTGAGGATTCCGACGATTCCCATAACAGCTTGTTACGACA
     GlyGluArgGlyPhePheTyrThrProLysAlaAlaLysGlyIleValGluGlnCysCys  124

ACCTCCATCTGCTCCTTGTACCAATTGGAAAACTACTGCAACTAGACGCAGCCCGCAGGC
1387 ---+---------+---------+---------+---------+---------+------ 1446
     TGGAGGTAGACGAGGAACATGGTTAACCTTTTGATGACGTTGATCTGCGTCGGGCGTCCG
     ThrSerIleCysSerLeuTyrGlnLeuGluAsnTyrCysAsn***    3'-GGGCGTCCG  138
```

Fig. 2a

```
       XbaI
       TCTAGAAACTAAGATTAATATAATTATATAAAAATATTATCTTCTTTTCTTTAT-3'
1447   ---+---------+---------+---------+---------+---------+      1500
       AGATCTTTGATTCTAATTATATTAATATATTTTTATAATAGAAGAAAAGAAATA-5'
       AGATCTTTGATTCTAATT-5'
             #2371
```

Fig. 2b

INSULIN DERIVATIVES

CROSS-REFERENCE TO RELATED APPLICATIONS

This application is a continuation of application Ser. No. 09/861,687 filed on May 21, 2001 now U.S. Pat. No. 6,620,780, which is a divisional of Ser. No. 08/932,082 filed on Sep. 17, 1997, now U.S. Pat. No. 6,251,856, which is a continuation of PCT/DK96/00107 filed Mar. 18, 1996, which is a continuation-in-part of Ser. No. 08/448,210, filed May 23, 1995, now abandoned, and claims priority under 35 U.S.C. 119 of Danish application 0276/95 filed Mar. 17, 1995, the contents of which are fully incorporated herein by reference.

FIELD OF THE INVENTION

The present invention relates to novel human insulin derivatives which are soluble and have a protracted profile of action, to a method of providing such derivatives, to pharmaceutical compositions containing them, and to the use of such insulin derivatives in the treatment of diabetes.

BACKGROUND OF THE INVENTION

Many diabetic patients are treated with multiple daily insulin injections in a regimen comprising one or two daily injections of a protracted insulin to cover the basal requirement supplemented by bolus injections of a rapid acting insulin to cover the meal-related requirements.

Protracted insulin compositions are well known in the art. Thus, one main type of protracted insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies (Samuel et al., Studies on the immunogenicity of protamines in humans and experimental animals by means of a micro-complement fixation test, Clin. Exp. Immunol. 33, pp. 252–260 (1978)).

Also, evidence has been found that the protamine-insulin complex is itself immunogenic (Kurtz et al., Circulating IgG antibody to protamine in patients treated with protamine-insulins. Diabetologica 25, pp. 322–324 (1983)). Therefore, with some patients the use of protracted insulin compositions containing protamines must be avoided.

Another type of protracted insulin compositions are solutions having a pH value below physiological pH from which the insulin will precipitate because of the rise in the pH value when the solution is injected. A drawback is that the solid particles of the insulin act as a local irritant causing inflammation of the tissue at the site of injection.

WO 91/12817 (Novo Nordisk A/S) discloses protracted, soluble insulin compositions comprising insulin complexes of cobalt(III). The protraction of these complexes is only intermediate and the bioavailability is reduced.

Human insulin has three primary amino groups: the N-terminal group of the A-chain and of the B-chain and the $\epsilon$-amino group of $Lys^{B29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group. No specifically $N^{\epsilon B29}$-substituted insulins are disclosed.

According to GB Patent No. 1.492.997 (Nat. Res. Dev. Corp.), it has been found that insulin with a carbamyl substitution at $N^{\epsilon B29}$ has an improved profile of hypoglycaemic effect.

P laid-open patent application No. 1-254699 (Kodama Co., Ltd.) discloses insulin wherein a fatty acid is bound to the amino group of $Phe^{B1}$ or to the $\epsilon$-amino group of $Lys^{B29}$ or to both of these. The stated purpose of the derivatisation is to obtain a pharmacologically acceptable, stable insulin preparation.

Insulins, which in the B30 position has an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or swine insulin antibodies.

U.S. Pat. No. 5,359,030 (Ekwuribe, Protein Delivery, Inc.) describes conjugation-stabilized polypeptide compositions for oral or parenteral administration comprising a polypeptide covalently coupled with a polymer including a linear polyalkylene moiety and a lipophilic moiety, said moieties being arranged so relative to each other that the polypeptide has an enhanced in vivo resistance to enzymatic degradation.

EP 511600 A2 relates i.a. to protein derivatives of the formula [protein][Z]$_n$, wherein [protein] represents a protein having n amino residues each derivable from an amino group by removal of one of its hydrogen atoms, in stead of amino groups, [Z] is a residue represented by the formula —CO—W—COOH wherein W is a divalent long chain hydrocarbon group which may also contain certain hetero atoms and n represents an average of the number of amide bonds between [Z] and [protein]. It is mentioned that the protein derivatives of the invention have an extremely prolonged serum half-life as compared with the proteins from which they are derived and that they exhibit no antigenicity. It is also mentioned, that insulin is one of the proteins from which derivatives according to the invention can be made, but no specific insulin derivatives are disclosed in EP 511600 nor is there any indication of a preferred [Z] or (a) preferred position(s) in which [Z] should be introduced in order to obtain useful insulin derivatives.

In the present specification, whenever the term insulin is used in a plural or a generic sense it is intended to encompass both naturally occurring insulins and insulin analogues and derivatives thereof. By "insulin derivative" as used herein is meant a polypeptide having a molecular structure similar to that of human insulin including the disulphide bridges between $Cys^{A7}$ and $Cys^{B7}$ and between $Cys^{A20}$ and $Cys^{B19}$ and an internal disulphide bridge between $Cys^{A6}$ and $Cys^{A11}$, and which have insulin activity.

However, there still is a need for protracted injectable insulin compositions which are solutions and contain insulins which stay in solution after injection and possess minimal inflammatory and immunogenic properties.

One object of the present invention is to provide human insulin derivatives, with a protracted profile of action, which are soluble at physiological pH values.

Another object of the present invention is to provide a pharmaceutical composition comprising the human insulin derivatives according to the invention.

It is a further object of the invention to provide a method of making the human insulin derivatives of the invention.

SUMMARY OF THE INVENTION

Surprisingly, it has turned out that certain insulin derivatives, wherein either the amino group of the N-terminal amino acid of the B-chain has a lipophilic substituent comprising from 12 to 40 carbon atoms attached, or wherein the carboxylic acid group of the C-terminal amino acid of the B-chain has a lipophilic substituent comprising from 12 to 40 carbon atoms attached, have a protracted profile of action and are soluble at physiological pH values.

Accordingly, in its broadest aspect, the present invention relates to an insulin derivative having the following sequence:

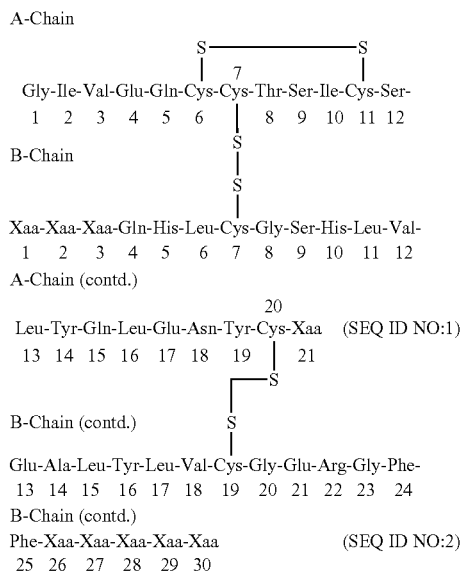

wherein

Xaa at position A21 is any codable amino acid except Lys, Arg and Cys;

Xaa at positions B1, B2, B3, B26, B27, B28 and B29 are, independent of each other, any codable amino acid except Cys or deleted;

Xaa at position B30 is any codable amino acid except Cys, a dipeptide comprising no Cys or Arg, a tripeptide comprising no Cys or Arg, a tetrapeptide comprising no Cys or Arg or deleted; and either the amino group of the N-terminal amino acid of the B-chain has a lipophilic group, W, attached to it which group has from 12 to 40 carbon atoms and optionally contains a group which can be negatively charged or the carboxyl group of the C-terminal amino acid of the B-chain has a lipophilic group, Z, attached to it which group has from 12 to 40 carbon atoms and optionally contains a group which can be negatively charged with the proviso that if one or more of the amino acids at position B1, B2 and B3 is (are) deleted then the number of the N-terminal amino acid is found by counting down from $Cys^{B7}$ which is always assigned the number 7 and that (a) when B1-B2-B3 is Phe-Val-Asn and A21 is Asn and B26-B27-B28-B29-B30 is Tyr-Thr-Pro-Lys-Thr (SEQ ID NO:3) or Tyr-Thr-Pro-Lys-Ala (SEQ ID NO:4), then said W or Z always contains a group which can be negatively charged; and (b) when B29 and B30 are deleted and a group Z as defined above is present at the C-terminal amino acid of the B-chain and neither B1, B2 nor B3 is deleted then B1-B2 is different from Phe-Val or B26-B27-B28 is different from Tyr-Thr-Pro or both B1-B2 and B26-B27-B28 are different from said sequences; and (c) when B29 and B30 are deleted and a group Z as defined above is present at the C-terminal amino acid of the B-chain and one of B1, B2 or B3 is deleted then the N-terminal amino acid of the B-chain is different from Val or the sequence B26-B27-B28 is different from Tyr-Thr-Pro or both the N-terminal amino acid of the B-chain and the sequence B26-B27-B28 are different from Val and Tyr-Thr-Pro respectively.

In a preferred embodiment, the present invention relates to an insulin derivative having the following sequence:

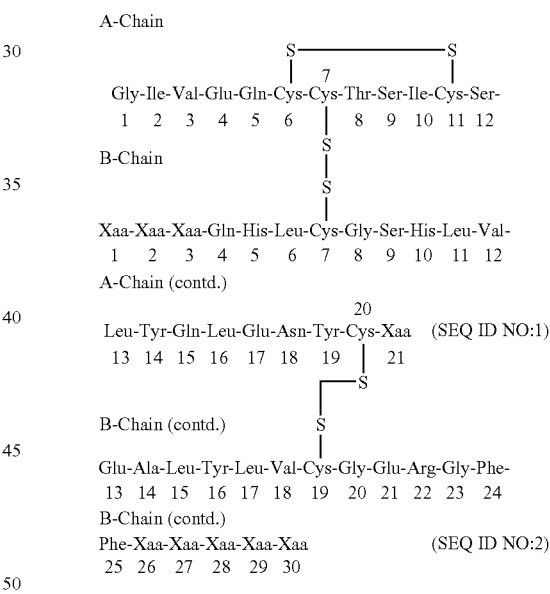

wherein

Xaa at position A21 is any codable amino acid except Lys, Arg and Cys;

Xaa at positions B1, B2, B3, B26, B27, B28, B29 and B30 are, independent of each other, any codable amino acid except Cys or deleted; and either the amino group of the N-terminal amino acid of the B-chain has a lipophilic group, W, attached to it which group has from 12 to 40 carbon atoms and optionally contains a group which can be negatively charged or the carboxyl group of the C-terminal amino acid of the B-chain has a lipophilic group, Z, attached to it which group has from 12 to 40 carbon atoms and optionally contains a group which can be negatively charged with the proviso that if one or more of the amino acids at position B1, B2 and B3 is (are) deleted then the number of the N-terminal amino acid is found by counting down from $Cys^{B7}$ which is always assigned the number 7 and that (a) when B1-B2-B3 is Phe-Val-Asn and A21 is Asn and B26-B27-B28-B29-B30 is Tyr-Thr-Pro-Lys-Thr or Tyr-Thr-Pro-Lys-Ala, then said W or Z always contains a group which can be negatively charged; and (b) when B29 and B30 are deleted and a group Z as defined above is present at the C-terminal amino acid of the B-chain and neither B1, B2 nor B3 is deleted then B1-B2 is different from Phe-Val or B26-B27-B28 is different from Tyr-Thr-Pro or both B1-B2 and B26-B27-B28 are different from said sequences; and (c) when B29 and B30 are deleted and a group Z as defined above is present at the C-terminal amino acid of the B-chain and one of B1, B2 or B3 is deleted then the N-terminal amino acid of the B-chain is different from Val or the sequence B26-B27-B28 is different from Tyr-Thr-Pro or both the N-terminal amino acid of the B-chain and the sequence B26-B27-B28 are different from Val and Tyr-Thr-Pro respectively.

When a lipophilic group, W, is attached to the α-amino group of the N-terminal amino acid of the B-chain, then the bond between the α-amino group and W is preferably an amide bond in which the N-terminal amino group of the B-chain constitutes the amine moiety and a group contained in W constitutes the carboxyl moiety.

When a lipophilic group, Z, is attached to the carboxyl group of the C-terminal amino acid of the B-chain, then the bond between the carboxyl group and Z is preferably an amide bond in which the C-terminal carboxyl group constitutes the carboxyl moiety and an amino group contained in Z constitutes the amine moiety.

In another preferred embodiment, the invention relates to an insulin derivative as described above wherein a lipophilic group, W, is attached to the α-amino group of the N-terminal amino acid of the B-chain.

In another preferred embodiment, the invention relates to a insulin derivative as described above wherein a lipophilic group, Z, is attached to the carboxyl group of the C-terminal amino acid of the B-chain.

In another preferred embodiment, the invention relates to an insulin derivative wherein the amino acid at position A21 is selected from the group comprising Ala, Asn, Gln, Glu, Gly and Ser.

In another preferred embodiment, the invention relates to an insulin derivative wherein the amino acid at position B1 is Phe.

In another preferred embodiment, the invention relates to an insulin derivative wherein the amino acid at position B1 is deleted.

In another preferred embodiment, the invention relates to an insulin derivative wherein the amino acid at position B2 is selected from the group comprising Ala and Val.

In another preferred embodiment, the invention relates to an insulin derivative wherein the amino acid at position B3 is selected from the group comprising Asn, Gln, Glu and Thr.

In another preferred embodiment, the invention relates to an insulin derivative wherein the amino acid at position B26 is Tyr.

In another preferred embodiment, the invention relates to an insulin derivative wherein the amino acid at position B27 is Thr.

In another preferred embodiment, the invention relates to an insulin derivative wherein the amino acid at position B28 is Pro.

In another preferred embodiment, the invention relates to an insulin derivative wherein the amino acid at position B29 is Lys or Thr.

In another preferred embodiment, the invention relates to an insulin derivative wherein the amino acid at position B28 is Lys and the amino acid at position B29 is Pro.

In another preferred embodiment, the invention relates to an insulin derivative wherein the amino acid at position B30 is Thr or ε-acylated Lys.

In another preferred embodiment, the invention relates to an insulin derivative wherein Xaa at position 30 in SEQ ID NO:2 designates the dipeptide Thr-Lys.

In another preferred embodiment, the invention relates to an insulin derivative wherein Xaa at position 30 in SEQ ID NO:2 designates the dipeptide Gly-Lys.

In another preferred embodiment, the invention relates to an insulin derivative wherein Xaa at position 30 in SEQ ID NO:2 designates the tripeptide Glu-Ser-Lys.

In another preferred embodiment, the invention relates to an insulin derivative wherein Xaa at position 30 in SEQ ID NO:2 designates the tripeptide Thr-Gly-Lys.

In another preferred embodiment, the invention relates to an insulin derivative wherein Xaa at position 30 in SEQ ID NO:2 designates the tetrapeptide Thr-Gly-Gly-Lys.

In another preferred embodiment, the invention relates to an insulin derivative wherein Xaa at position 30 in SEQ ID NO:2 designates the tetrapeptide Thr-Glu-Gly-Lys.

In another preferred embodiment, the invention relates to an insulin derivative wherein Xaa at position 30 in SEQ ID NO:2 designates the tetrapeptide Gly-Asp-Thr-Lys.

In another preferred embodiment, the invention relates to an insulin derivative wherein the C-terminal amino acid of the B-chain is ε-acylated Lys and the amino acid next to the C-terminal amino acid is Gly.

In another preferred embodiment, the invention relates to an insulin derivative wherein the parent insulin is a des(B30) insulin.

In another preferred embodiment, the invention relates to an insulin derivative wherein the parent insulin is des(B30) human insulin.

In another preferred embodiment, the invention relates to an insulin derivative wherein the parent insulin is a des (B28–B30) insulin.

In another preferred embodiment, the invention relates to an insulin derivative wherein the parent insulin is a des (B27–B30) insulin.

In another preferred embodiment, the invention relates to an insulin derivative wherein the parent insulin is a des (B26–B30) insulin.

In another preferred embodiment, the invention relates to an insulin derivative wherein the amino acid at position B28 is Pro and the amino acid at position B29 is Thr.

In another preferred embodiment, the invention relates to an insulin derivative which has a group, W, as mentioned above, attached to the N-terminal α-amino group of its B-chain, W being a group of the general formula $CH_3(CH_2)_n CH(COOH)NH—CO(CH_2)_2CO—$ wherein n is an integer from 9 to 15.

In another preferred embodiment, the invention relates to an insulin derivative which has a group, W, as mentioned above, attached to the N-terminal α-amino group of its B-chain, W being a group of the general formula $CH_3(CH_2)_r CO—NHCH(COOH)(CH_2)_2CO—$ wherein r is an integer from 9 to 15.

In another preferred embodiment, the invention relates to an insulin derivative which has a group, W, as mentioned above, attached to the N-terminal α-amino group of its B-chain, W being a group of the general formula $CH_3(CH_2)_3$ CO—NHCH((CH2)$_2$COOH)CO— wherein s is an integer from 9 to 15.

In another preferred embodiment, the invention relates to an insulin derivative which has a group, Z, as mentioned above, attached to the C-terminal amino acid of its B-chain, wherein Z is a group of the general formula —NHCH (COOH)(CH$_2$)$_4$NH—CO(CH$_2$)$_m$CH$_3$ wherein m is an integer from 8 to 18, that is, Z is a $N^\epsilon$-acylated lysine residue.

In another preferred embodiment, the invention relates to an insulin derivative which has a group, Z, as mentioned above, attached to the C-terminal amino acid of its B-chain, wherein Z is a group of the general formula —NHCH (COOH)(CH$_2$)$_4$NH—COCH((CH$_2$)$_2$COOH)NH—CO (CH$_2$)$_p$CH$_3$ wherein p is an integer from 10 to 16.

In another preferred embodiment, the invention relates to an insulin derivative which has a group, Z, as mentioned above, attached to the C-terminal amino acid of its B-chain, wherein Z is a group of the general formula —NHCH (COOH)(CH$_2$)$_4$NH—CO(CH$_2$)$_2$CH(COOH)NH—CO (CH$_2$)$_q$CH$_3$ wherein q is an integer from 10 to 16.

In another preferred embodiment, the invention relates to an insulin derivative which has a group, Z, as mentioned above, which comprises a partly or completely hydrogenated cyclopentanophenanthrene skeleton.

In another preferred embodiment, the invention relates to an insulin derivative which has a group, Z, as mentioned above, which is an acylated amino acid, in particular acylated lysine.

In another preferred embodiment, the invention relates to Thr$^{B29}$ human insulin with a group Z as described above attached to the C-terminal amino acid of its B-chain.

In another preferred embodiment, the invention relates to des(B28–B30) human insulin with a group Z as described above attached to the C-terminal amino acid of its B-chain.

In another preferred embodiment, the invention relates to des(B27–B30) human insulin with a group Z as described above attached to the C-terminal amino acid of its B-chain.

In another preferred embodiment, the invention relates to des(B26–B30) human insulin with a group Z as described above attached to the C-terminal amino acid of its B-chain.

In another preferred embodiment, the invention relates to the use of an insulin derivative according to the invention for the preparation of a medicament for treating diabetes.

In another preferred embodiment, the invention relates to a pharmaceutical composition for the treatment of diabetes in a patient in need of such a treatment comprising a therapeutically effective amount of an insulin derivative according to the invention together with a pharmaceutically acceptable carrier.

In another preferred embodiment, the invention relates to a pharmaceutical composition for the treatment of diabetes in a patient in need of such a treatment comprising a therapeutically effective amount of an insulin derivative according to the invention, in mixture with an insulin or an insulin analogue which has a rapid onset of action, together with a pharmaceutically acceptable carrier.

In another preferred embodiment, the invention relates to a pharmaceutical composition comprising an insulin derivative according to the invention which is soluble at physiological pH values.

In another preferred embodiment, the invention relates to a pharmaceutical composition comprising an insulin derivative according to the invention which is soluble at pH values in the interval from about 6.5 to about 8.5.

In another preferred embodiment, the invention relates to a protracted pharmaceutical composition comprising an insulin derivative according to the invention.

In another preferred embodiment, the invention relates to a pharmaceutical composition which is a solution containing from about 120 nmol/ml to about 1200 nmol/ml, preferably about 600 nmol/ml of an insulin derivative according to the invention.

In another preferred embodiment, the invention relates to a method of treating diabetes in a patient in need of such a treatment comprising administering to the patient a therapeutically effective amount of an insulin derivative according to this invention together with a pharmaceutically acceptable carrier.

In another preferred embodiment, the invention relates to a method of treating diabetes in a patient in need of such a treatment comprising administering to the patient a therapeutically effective amount of an insulin derivative according to this invention, in mixture with an insulin or an insulin analogue which has a rapid onset of action, together with a pharmaceutically acceptable carrier.

Examples of preferred insulin derivatives according to the present invention are the following:
($N^{\epsilon B30}$-tetradecanoyl) Thr$^{B29}$,Lys$^{B30}$ human insulin,
($N^{\epsilon B28}$-tetradecanoyl) Lys$^{B28}$ des(B29,B30) human insulin,
($N^{\epsilon B27}$-tetradecanoyl) Lys$^{B27}$ des(B28–B30) human insulin and
($N^{\epsilon B26}$-tetradecanoyl) Lys$^{B26}$ des(B27–B30) human insulin.
($N^{\epsilon B32}$-tetradecanoyl) Glu$^{B30}$,Ser$^{B31}$,Lys$^{B32}$ human insulin.
($N^{\epsilon B29}$-acetyl,$N^{\epsilon B32}$-tetradecanoyl) Glu$^{B30}$,Ser$^{B31}$,Lys$^{B32}$ human insulin.

BRIEF DESCRIPTION OF THE DRAWINGS

The present invention is further illustrated with reference to the appended drawing wherein:

FIG. 2a which is continued in FIG. 2b shows the sequence of pMT742, position 907 to 1500, and the oligonucleotides #94, #593, #2371 and #3075 used for PCR1A, PCR1B and PCR1C of Example 1. The 138 amino acid sequence corresponding to the MF alpha prepro-leader (amino acids Nos. 1–85) and an insulin precursor which has the amino acid sequence B(1–29)AlaAlaLysA(1–21) wherein A(1–21) is the A chain of human insulin and B(1–29) is the B chain of human insulin in which Thr(B30) is missing, is shown below the coding sequence (amino acids Nos. 86–138).

DETAILED DESCRIPTION OF THE INVENTION

Terminology

Figure 1:
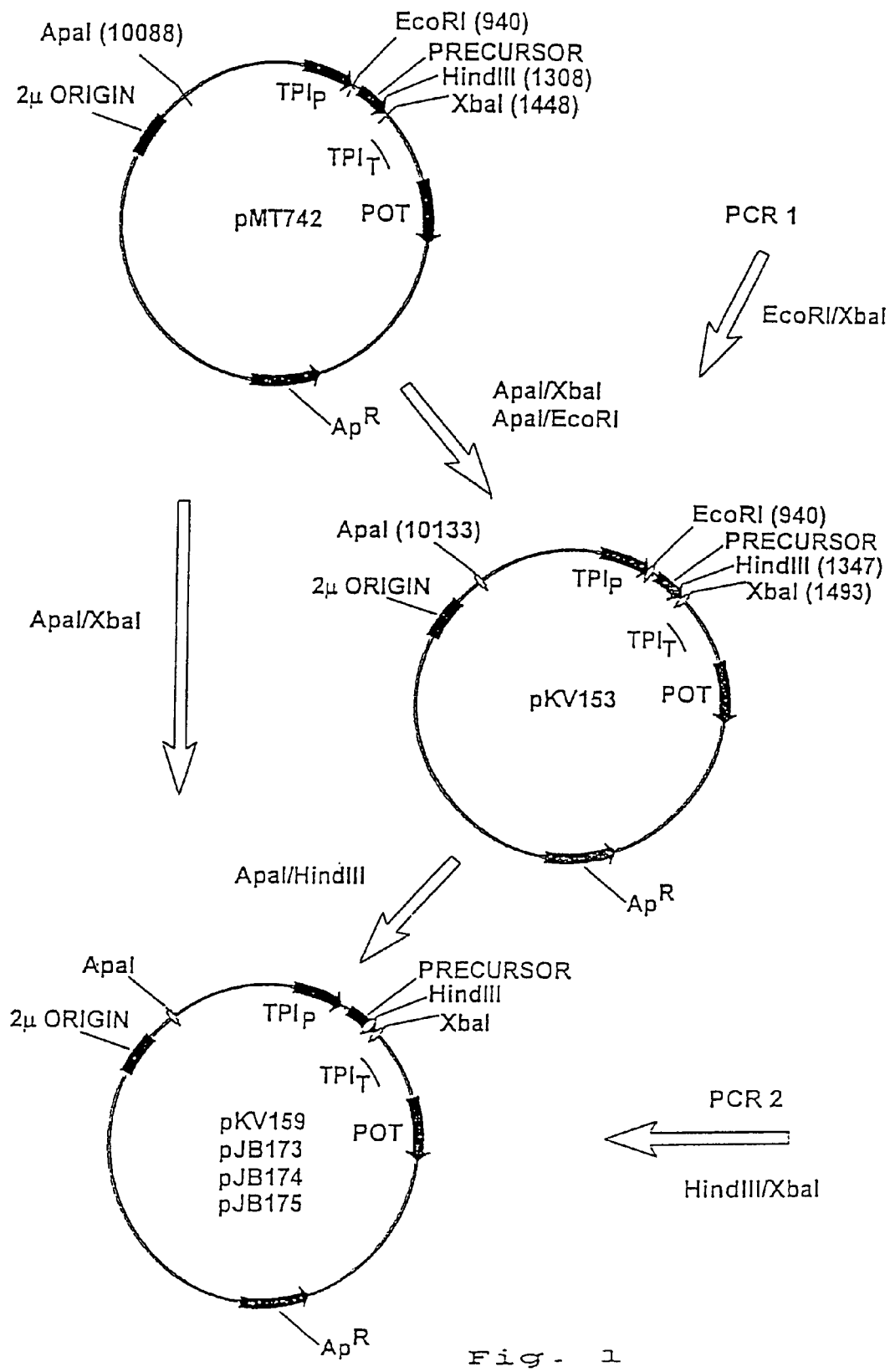
FIG. 1 shows the construction of the plasmids pKV153, pKV159, pJB173, pJB174 and pJB175.

The three letter codes and one letter codes for the amino acid residues used herein are those stated in J. Biol. Chem. 243, p. 3558 (1968).

In the DNA sequences, A is adenine, C is cytosine, G is guanine, and T is thymine. The following acronyms are used:
DMSO for dimethyl sulphoxide,
DMF for dimethylformamide,
Boc for tert-butoxycarbonyl,
NMP for 1-methyl-2-pyrrolidone,
TFA for trifluoroacetic acid,
X—OSu for an N-hydroxysuccinimid ester,
X for an acyl group, RP-HPLC for reversed phase high performance liquid chromatography.

Preparation of Lipophilic Insulin Derivatives

The insulin derivatives according to the present invention can be prepared i.a. as described in the following:

1. Insulin Derivatives Featuring in Position B30 an Amino Acid Residue which can be Coded for by the Genetic Code, e.g. Threonine (Human Insulin) or Alanine (Porcine Insulin).

1.1 Insulins Modified by Attachment of a Lipophilic Group, W, to the N-terminal Amino Group, Starting from Human Insulin.

Human insulin is treated with a Boc-reagent (e.g. di-tert-butyl dicarbonate) to form (A1,B29)-diBoc human insulin, i.e., human insulin in which the N-terminal end of the A-chain and the ε-amino group of $Lys^{B29}$ are protected by a Boc-group. After an optional purification, e.g. by HPLC, an acyl group is introduced in the α-amino group of $Phe^{B1}$ by allowing the product to react with a N-hydroxysuccinimide ester of the formula W—OSu wherein W is an acyl group as defined in the above to be introduced at the N-terminal α-amino group of the B-chain. In the final step, TFA is used to remove the Boc-groups and the product, $N^{\alpha B1}$—W human insulin, is isolated.

2. Insulin Derivatives with no Amino Acid Residue in Position B30. i.e. des(B30) Insulins.

2.1 Starting from Human Insulin or Porcine Insulin.

On treatment with carboxypeptidase A in ammonium buffer, human insulin and porcine insulin both yield des(B30) insulin. After an optional purification, the des(B30) insulin is treated with a Boc-reagent (e.g. di-tert-butyl dicarbonate) to form (A1,B29)-diBoc des(B30) insulin. After an optional purification, e.g. by HPLC, an acyl group is introduced in the α-amino group of the amino acid in position B1 by allowing the product to react with a N-hydroxysuccinimide ester of the formula W—OSu wherein W is the acyl group to be introduced. In the final step, TFA is used to remove the Boc-groups and the product, ($N^{\alpha B1}$—W) des(B30) insulin, is isolated.

2.2 Starting from a Single Chain Human Insulin Precursor.

A single chain human insulin precursor, which is extended in position B1 with an extension (Ext) which is connected to B1 via an arginine residue and which has a bridge from a C-terminal lysine in position B26, B27, B28 or B30 to A1 can be a used as starting material. Preferably, the bridge is a peptide of the formula $Y_n$-Arg, where Y is a codable amino acid except cysteine, lysine and arginine, and n is zero or an integer between 1 and 35. When n>1, the Y's may designate different amino acids. Preferred examples of the bridge from Lys in position B26, B27, B28 or B30 to A1 are: AlaAlaArg, SerArg, SerAspAspAlaArg (SEQ ID NO:5) and Arg (European Patent No. 163529). Treatment of such a precursor of the general formula Ext-Arg-B(1–Q)-$Y_n$-Arg-A(1–21), wherein Q is 26, 27, 28 or 30, with a lysyl endopeptidase, e.g. *Achromobacter lyticus* protease, yields Ext-Arg-B(1–Q) $Y_n$-Arg-A(1–21) insulin. Acylation of this intermediate with a N-hydroxysuccinimide ester of the general formula X—OSu wherein X is an acyl group, introduces the acyl group X in the ε-amino group of $Lys^{BQ}$, and in the N-terminal amino group of the A-chain and the B-chain to give ($N^{\epsilon BQ}$-X) X-Ext-Arg-B(1–Q) X-$Y_n$-Arg-A(1–21) insulin. This intermediate on treatment with trypsin in mixture of water and a suitable organic solvent, e.g. DMF, DMSO or a lower alcohol, gives the desired derivative, Z-human insulin wherein Z is $Lys^{\epsilon BQ}$-X.

Pharmaceutical Compositions

Pharmaceutical compositions containing a human insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the human insulin derivative in the form of a nasal spray.

Pharmaceutical compositions containing a compound of the present invention may be prepared by conventional techniques, e.g. as described in *Remington's Pharmaceutical Sciences*, 1985.

Thus, the injectable human insulin compositions of the invention can be prepared using the conventional techniques of the pharmaceutical industry which involves dissolving and mixing the ingredients as appropriate to give the desired end product.

Thus, according to one procedure, the human insulin derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Preferred pharmaceutical compositions of the particular insulins of the present invention are solutions hexameric complexes. Typically the hexameric complexes are stabilized by two or more zinc ions and three or more molecules of a phenolic compound like phenol or meta-cresol or mixtures thereof per hexamer.

In a particular embodiment, a composition is provided which contains two different insulins, one having a protracted profile of action and one having a rapid onset of action, in the form of soluble hexameric complexes. Typically the hexameric complexes are stabilized by two or more zinc ions and three or more molecules of a phenolic compound like phenol or meta-cresol or mixtures thereof per hexamer. The complexes are mixtures of hexamers of the particular insulins and mixed hexamers in which the ratio between the two different insulins is from 1:5 to 5:1.

A composition for nasal administration of an insulin derivative according to the present invention may, for example, be prepared as described in European Patent No. 272097 (to Novo Nordisk A/S).

The insulin compositions of this invention can be used in the treatment of diabetes. The optimal dose level for any patient will depend on a variety of factors including the efficacy of the specific human insulin derivative employed, the age, body weight, physical activity, and diet of the patient, on a possible combination with other drugs, and on the severity of the case of diabetes. It is recommended that the daily dosage of the human insulin derivative of this invention be determined for each individual patient by those skilled in the art in a similar way as for known insulin compositions.

Where expedient, the human insulin derivatives of this invention may be used in mixture with other types of insulin, e.g. human insulin or porcine insulin or insulin analogues with a more rapid onset of action. Examples of such insulin analogues are described e.g. in the European patent applications having the publication Nos. EP 214826 (Novo Nordisk is A/S), EP 375437 (Novo Nordisk A/S) and EP 383472 (Eli Lilly & Co.).

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Plasmids and DNA Material

All expression plasmids are of the cPOT type. Such plasmids are described in EP patent application No. 171 142 and are characterised in containing the *Schizosaccharomyces pombe* triose phosphate isomerase gene (POT) for the purpose of plasmid selection and stabilisation. A plasmid containing the POT-gene is available from a deposited *E. coli* strain (ATCC 39685). The plasmids furthermore contain the *S. cerevisiae* triose phosphate isomerase promoter and terminator ($P_{TPI}$ and $T_{TPI}$). They are identical to pMT742 (Egel-Mitani, M et al., *Gene* 73 (1988) 113–120) (see FIG. 1) except for the region defined by the EcoRI-XbaI restriction sites encompassing the coding region for MF alpha prepro leader/product. The EcoRI/XbaI fragment of pMT742 itself encodes the Mating Factor (MF) alpha pre-pro-leader sequence of *Saccharomyces cerevisiae* followed by the insulin precursor MI3 which has a Ala-Ala-Lys bridge connecting B29 and A1 (i.e. B(1–29)-Ala-Ala-Lys-A(1–21)) (see FIG. 2)

Synthetic DNA fragments were synthesised on an automatic DNA synthesizer (Applied Biosystems model 380A) using phosphoramidite chemistry and commercially available reagents (Beaucage, S. L. and Caruthers, M. H., *Tetrahedron Letters* 22 (1981) 1859–1869).

All other methods and materials used common state of the art knowledge (see, e.g. Sambrook, J., Fritsch, E. F. and Maniatis, T. *Molecular Cloning: A Laboratory Manual*, Cold Spring Harbour Laboratory Press, New York, 1989).

Analytical

Molecular masses of insulin precursors prepared were obtained by mass spectroscopy (MS), either by plasma desorption mass spectrometry (PDMS) using Bio-Ion 20 instrument (Bio-Ion Nordic AB, Uppsala, Sweden) or electrospray mass spectrometry (ESMS) using an API III Biomolecular Mass Analyzer (Perkin Elmer Sciex Instruments, Thornhill, Canada).

The lipophilicity of an insulin derivative relative to human insulin, $k'_{rel}$, was measured on a LiChrosorb® RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water. The elution was monitored by the absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}$ is defined as $(t_{derivative}-t_0)/(t_{hyman}-t_0)$.

As a measure of the protraction of the compounds of the invention, the disappearance rate in pigs was studied and $T_{50\%}$ was determined. $T_{50\%}$ is the time when 50% of the A14 Tyr($^{125}$I)-labeled analogue has disappeared from the site of injection as measured with an external γ-counter (Ribel, U et al., The Pig as a Model for Subcutaneous Absorption in Man. In: M. serrano-Rios and P. J. Lefebre (Eds): Diabetes 1985; Proceedings of the 12th Congress of the International Diabetes Federation, Madrid, Spain, 1985 (Excerpta Medica, Amsterdam, (1986) 891–96).

Example 1

Synthesis of Glu-Glu-Ala-Glu-Ala-Glu-Ala-Glu-Pro-Lys-Ala-Thr-Arg-B(1–29)-Ser-Asp-Asp-Ala-Arg-A(1–21) insulin precursor (SEQ ID NO:6-B(1–29)-SEQ ID NO:5-A (1–21)) from yeast strain yKV153 using the *S.cerevisiae* MF alpha prepro-leader.

The following oligonucleotides were synthesised:

(SEQ ID NO:9)
593 5'-CCAAGTACAAAGCTTCAACCAAGTGGGAACCGCACAAGTGT

TGGTTAACGAATCTTGTAGCCTTTGGTTCAGCTTCAGCTTCAGC

TTCTTCTCTTTTATCCAAAGAAACACC-3'

(SEQ ID NO:10)
94 5'-TAAATCTATAACTACAAAAAACACATA-3'

(SEQ ID NO:11)
3075 5'-TTGGTTGAAGCTTTGTACTTGGTTTGCGGTGAAAGAGGTTT

CTTCTACACTCCTAAGTCTGACGATGCTAGAGGTATTG-3'

(SEQ ID NO:12)
2371 5'-TTAATCTTAGTTTCTAGAGCCTGCGGG-3'

The following two Polymerase Chain Reactions (PCR) were performed using Gene Amp PCR reagent kit (Perkin Elmer, 761 Main Avewalk, CT, USA) according to the manufacturer's instructions (see FIG. 2).

PCR1A:
0.2 μl of pMT742 plasmid template
4.0 μl of oligonucleotide #593 (100 pmol)
4.0 μl of oligonucleotide #94 (100 pmol)
10.0 μl of 1O×PCR buffer
10.0 μl of 2.5 Mm dNTP
0.5 μl of Taq polymerase enzyme
71.3 μl of water PCR1B:
0.2 μl of pMT742 plasmid template
4.0 μl of oligonucleotide #3075 (100 pmol)
4.0 μl of oligonucleotide #2371 (100 pmol)
10.0 μl of 1O×PCR buffer
10.0 μl of 2.5 mM dNTP
0.5. μl of Taq polymerase enzyme
71.3 μl of water In both cases two cycles were performed at 94° C. for 1 min., 45° C. for 1 min. and 72° C. for 1 min. and subsequently followed by 11 cycles: 94° C. for 1 min., 55° C. for 1 min., 72° C. for 1 min.

20 μl of each PCR mixture was loaded onto a 2% agarose gel and subjected to electrophoresis using standard techniques (Sambrook et al., Molecular cloning, Cold Spring Harbour Laboratory Press, 1989). Resulting DNA fragments (452 bp from PCR1A and 170 bp from PCR1B) were cut out of the agarose gel and isolated using the Gene Clean kit (Bio101 Inc., PO BOX 2284, La Jolla, Calif., USA) according to the manufacturer's instructions. The purified DNA fragments were dissolved in 100 μl of water.

The following PCR was performed

PCR1C:
1.0 μl of DNA fragment from PCR1A
1.0 μL of DNA fragment from PCR1B
10.0 μl of 10×PCR buffer
10.0 μl of 2.5 mM dNTP
0.5 μl of Taq polymerase enzyme
69.5 μl of water Two cycles were performed at 94° C. for 1 min., 45° C. for 1 min. and 72° C. for 1 min.

Subsequently 4 μl of oligonucleotide #94 (100 pmol) and 4.0 μl of oligonucleotide #2371 (100 pmol) was added and 15 cycles were performed at 94° C. for 1 min., 55° C. for 1 min. and 72° C. for 1 min.

The PCR mixture was loaded onto a 1% agarose gel and the resulting 594 bp fragment was purified using the Gene Clean kit as described. The purified PCR DNA fragment was dissolved in 20 μl of water and restriction endonuclease buffer and cut with the restriction endonucleases EcoRI and XbaI (New England Biolabs, Inc. Mass., USA). The resulting 550 bp EcoRI/XbaI restriction fragment was run on agarose gel and isolated and purified using the Gene clean kit.

In two separate restriction endonuclease digestions the plasmid pMT742 was cut with i) restriction endonucleases ApaI and XbaI and ii) with restriction endonucleases ApaI and EcoRI. From these digestions the 8.6 kb ApaI/XbaI restriction fragment and the 2.1 kb ApaI/EcoRI restriction fragment was isolated.

The three fragments (i.e. the 550 bp EcoRI/XbaI restriction fragment from PCR1C and the 8.6 kb ApaI/XbaI restriction fragment and 2.1 kb ApaI/EcoRI restriction fragment from pMT742) were ligated together using T4 DNA ligase and standard conditions (Sambrook et al., Molecular cloning, Cold Spring Harbour Laboratory Press, 1989) (see FIG. 1). The ligation mixture was transformed into competent $E.\ coli$ cells (Ap$^{r-}$) followed by selection for ampicillin resistance. Plasmids were isolated from the resulting $E.\ coli$ colonies using standard DNA miniprep technique (Sambrook et al., Molecular cloning, Cold Spring Harbour Laboratory Press, 1989) and checked with appropriate restriction endonucleases (i.e. EcoRI, ApaI and XbaI). The selected plasmid designated pKV153 was shown by DNA sequencing analysis (using the Sequenase kit from U.S. Biochemical Corp, according to the manufacturer's recommendations) to contain the correct sequence encoding the MF alpha preproleader/Glu-Glu-Ala-Glu-Ala-Glu-Ala-Glu-Pro-Lys-Ala-Thr-Arg-B(1–29)-Ser-Asp-Asp-Ala-Arg-A(1–21) insulin precursor.

pKV153 was transformed into $S.\ cerevisiae$ strain MT663 and selected for growth on glucose as described in European patent application having the publication No. 214826.

The resulting yeast strain was designated yKV153 and was verified to produce Glu-Glu-Ala-Glu-Ala-Glu-Ala-Glu-Pro-Lys-Ala-Thr-Arg-B(1–29)-Ser-Asp-Asp-Ala-Arg-A (1–21) insulin precursor (SEQ ID NO:6-B(1–29)-SEQ ID NO:5-A(1–21)) in the culture media by HPLC and mass spectroscopy.

Example 2

Synthesis of Lys$^{B30}$(N$^\epsilon$-tetradecanoyl) Thr$^{B29}$ human insulin.

2a. Synthesis of Glu-Glu-Ala-Glu-Ala-Glu-Ala-Glu-Pro-Lys-Ala-Thr-Arg-B(1–28)-Thr-Lys-Ser-Asp-Asp-Ala-Arg-A(1–21) (SEQ ID NO:6-B(1–29)-SEQ ID NO:5-A(1–21)) insulin precursor from teast strain yKV159 using the $S.\ cerevisiae$ MF alpha prepro-leader.

The following oligonucleotides were synthesised:

(SEQ ID NO:13)
3881 5'-TTGGTTGAAGCTTTGTACTTGGTTTGCGGTGAAAGAGGTT

TCTTCTACACTCCTACCAAGTCTGACGATGCTAGAGGTATTGT

CG-3'

(SEQ ID NO:12)
2371 5'-TTAATCTTAGTTTCTAGAGCCTGCGGG-3'

The following Polymerase Chain Reaction (PCR) was performed using Gene Amp PCR reagent kit as described above.

PCR2:
0.2 μl of pKV153 plasmid template (from Example 1)
4.0 μl of oligonucleotide #3881 (100 pmol)
4.0 μl of oligonucleotide #2371 (100 pmol)
10.0 μl of 10×PCR buffer
10.0 μl of 2.5 mM dNTP
0.5 μl of Taq polymerase enzyme
71.3 μl of water Two cycles were performed at 94° C. for 1 min., 45° C. for 1 min. and 72° C. for 1 min. and subsequently followed by 11 cycles at 94° C. for 1 min., 55° C. for 1 min., 72° C. for 1 min.

The PCR mixture was loaded onto a 2% agarose gel and the resulting 174 bp fragment was purified using the Gene Clean kit as described. The purified PCR DNA fragment was dissolved in 20 μl of water and restriction endonuclease buffer and cut with the restriction endonucleases HindIII and XbaI. The resulting 153 bp HindIII/XbaI restriction fragment was run on agarose gel and isolated and purified using the Gene Clean kit.

In two separate restriction endonuclease digestions pMT742 was cut with restriction endonucleases ApaI and XbaI whereas pKV153 (from Example 1) was cut with restriction endonucleases ApaI and EcoRI. From this digestions the 8.6 kb ApaI/XbaI restriction fragment from pMT742 and the 2.1 kb ApaI/EcoRI restriction fragment from pKV153 was isolated.

The three fragments (i.e. the 550 bp EcoRI/XbaI restriction fragment from PCR2 and the 8.6 kb ApaI/XbaI restriction fragment from pMT748 and the 2.1 kb ApaI/EcoRI restriction fragment from pKV153) were ligated together using T4 DNA ligase as described above (see FIG. 1). The ligation mixture was transformed into competent $E.\ coli$ cells (Ap$^{r-}$) followed by selection for ampicillin resistance. Plasmids were isolated from the resulting $E.\ coli$ colonies and checked for appropriate restriction endonucleases (i.e. HindIII, ApaI and XbaI) as described.

The selected plasmid designated pKV159 was shown by DNA sequencing analysis to contain the correct sequence encoding the MF alpha prepro-leader/Glu-Glu-Ala-Glu-Ala-Glu-Ala-Glu-Pro-Lys-Ala-Thr-Arg-B(1–28)-Thr-Lys-Ser-Asp-Asp-Ala-Arg-A(1–21) insulin precursor (SEQ ID NO:6-B(1–28)-SEQ ID NO:7- A(1–21)).

pKV159 was transformed into $S.\ cerevisiae$ strain MT663 and selected for growth on glucose as described.

The resulting yeast strain was designated yKV159 and was verified to produce Glu-Glu-Ala-Glu-Ala-Glu-Ala-Glu-Pro-Lys-Ala-Thr-Arg-B(1–28)-Thr-Lys-Ser-Asp-Asp-Ala- Arg-A(1–21) insulin precursor (SEQ ID NO:6-B(1–29)-SEQ ID NO:5- A(1–21)) in the culture media by HPLC and mass spectroscopy.

2b. Isolation of Glu-Glu-Ala-Glu-Ala-Glu-Ala-Glu-Pro-Lys-Ala-Thr-Arg-B(1–28)-Thr-Lys-Ser-Asp-Asp-Ala-Arg-A(1–21) insulin precursor.

The yKV159 strain was fermented for 72 hours and five litres of broth were collected. Yeast cells were removed by centrifugation, the pH value was adjusted to 3.0 using sulphuric acid and the insulin precursor was concentrated on a Pharmacia Strealine® 50 column packed with 300 ml of Streamline® SP ion exchanger. After wash with 25 mM citrate buffer, pH value 3.6, the precursor was eluted by 0.5 M NH$_3$ and the fraction from 300 to 600 ml was collected. The pH value was adjusted to 2.5 and the precursor was purified by RP-HPLC using 15µ spherical C18 silica of 100 Å pore size and 0.2 M Na$_2$SO$_4$, 0.04 M H$_3$PO$_4$ as buffer, and using a gradient from 23 to 33% acetonitrile. The precursor eluted at about 27–28% acetonitrile. The pool containing the central major peak of the precursor was desalted by gel filtration on Sephadex® G-50 F in 0.5 M acetic acid, and the precursor isolated by lyophilization. Yield: 486 mg.

2c. Synthesis of Ala-Thr-Arg-B(1–28)-Thr-Lys, Ser-Asp-Asp-Ala-Arg-A(1 –21) insulin.

The 486 mg of single-chain precursor obtained as described above were dissolved in 30 ml of 0.05 M glutamate buffer at pH 9.0, and 3 ml of immobilized *A. lyticus* protease gel were added (see PCT/DK94/00347, page 45). After gentle stirring for 5 hours at 30° C., the gel was removed by filtration and the double-chain, extended insulin was crystallized by the addition of 10 ml of ethanol, 845 mg of trisodium citrate dihydrate and 78 mg of zinc chloride. After adjustment of the pH value to 6.1 and storage at 4° C. overnight the crystals were collected by centrifugation, washed twice with isopropanol and dried in vacuo. Yield: 450 mg.

2d. Synthesis of $N^{\alpha A-5},N^{\alpha B-3},N^{\epsilon B30}$-tris(tetradecanoyl) Ala-Thr-Arg-B(1–28)-Thr-Lys, Ser-Asp-Asp-Ala-Arg-A(1–21) insulin.

450 mg of the double-chain, extended insulin, obtained as described above, were dissolved in a mixture of 3.15 ml of DMSO and 0.69 ml of 2 M diisopropylethylamine in NMP. The solution was cooled to 15° C. and 0.69 ml of 0.3 M tetradecanoic acid N-hydroxysuccinimide ester in DMSO/NMP (1:1, v/v) was added. After 2 hours at 15° C., the reaction was stopped by addition of 112 ml of 0.01 M glycine buffer in ethanol/water (60:40, v/v) and the pH value adjusted to 10.0. The triacylated intermediate was not isolated.

2e. Synthesis of Lys$^{B30}$(N$^\epsilon$-tetradecanoyl) Thr$^{B29}$ human insulin.

To the solution from the previous step was added 5 ml of immobilized trypsin gel (see PCT/DK94/00347, page 46). After gentle stirring at 15° C. for 16 hours, the gel was removed by filtration, the pH value was adjusted to 9.0 and the solution was applied to a 2.5×25 cm column of QAE-Sephadex® A-25. Isocratic elution was performed at a rate of 17.3 ml/h using a 0.12 M NH$_4$Cl buffer in ethanol/water (60:40, v/v) adjusted to pH 9.0 with NH$_3$.

The title compound emerged from the column after 650 ml, and a pool from 650 to 754 ml was collected. Finally, the buffer was changed to 0.01 M NH$_4$HCO$_3$ by gel filtration on Sephadex® G-50 Fine, and the product isolated in the dry state by lyophilization. Yield: 91 mg.

Molecular mass of the title compound, found by MS: 6020±6, theory: 6018.

Molecular mass of the B-chain, found by MS: 3642±5, theory: 3640.

Molecular mass of the C-terminal fragment of B-chain digested by V8 protease, found by MS: 1326±2, theory: 1326.

Relative lipophilicity, k'$_{rel}$=113.

Disappearance half-life, T$_{50\%}$, after subcutaneous injection in pigs: 20.3±5.2 hours (n=6).

Example 3

Synthesis of Lys$^{B28}$(N$^\epsilon$-tetradecanoyl) des(B29-B30) human insulin.

3a. Synthesis of Glu-Glu-Ala-Glu-Ala-Glu-Ala-Glu-Pro-Lys-Ala-Thr-Arg-B(1–27)-Lys-Ser-Asp-Asp-Ala-Arg-A(1–21) insulin precursor (SEQ ID NO:6-B(1–27)-SEQ ID NO:8-A(1–21)) from yeast strain yJB173 using the *S. cerevisiae* MF alpha prepro-leader.

The following oligonucleotides were synthesised:

```
                                           (SEQ ID NO:14)
#627  5'-CACTTGGTTGAAGCTTTGTACTTGGTTTGCGGTGAAAGAGG

TTTCTTCTACACTAAGTCTGACGATGCTAG-3'
                                           (SEQ ID NO:12)
2371 5'-TTAATCTTAGTTTCTAGAGCCTGCGGG-3'
```

The DNA encoding Glu-Glu-Ala-Glu-Ala-Glu-Ala-Glu-Pro-Lys-Ala-Thr-Arg-B(1–27)-Lys-Ser-Asp-Asp-Ala-Arg-A(1–21) (SEQ ID NO:6-B(1–27)-SEQ ID NO:8-A(1–21)) was constructed in the same manner as described in Example 2 by substituting oligonucleotide #3881 with oligonucleotide #627.

The resulting plasmid was designated pJB173 and the yeast strain expressing Glu-Glu-Ala-Glu-Ala-Glu-Ala-Glu-Pro-Lys-Ala-Thr-Arg-B(1–27)-Lys-Ser-Asp-Asp-Ala-Arg-A(1–21) (SEQ ID NO:6-B(1–27)-SEQ ID NO:8-A(1–21)) was designated yJB173.

3b . Isolation of Glu-Glu-Ala-Glu-Ala-Glu-Ala-Glu-Pro-Lys-Ala-Thr-Arg-B(1–27)-Lys-Ser-Asp-Asp-Ala-Arg-A(1–21) insulin precursor.

The yJB173 strain was fermented for 72 hours and 4.8 liters of broth were collected. Yeast cells were removed by centrifugation and the pH value was adjusted to 3.0 using sulphuric acid. The conductivity was 7.8 mS/cm. The insulin precursor was concentrated using a Pharmacia Streamline® 50 column packed with 300 ml of Streamline® SP ion exchanger. After wash with 25 mM citrate buffer, pH value 3.6, the precursor was eluted by 0.5 M NH$_3$ and the fraction from 300 to 600 ml was collected. Free ammonia was evaporated in vacuo at room temperature and the pH value of the resulting 280 ml of solution was adjusted to 9.0 with hydrochloric acid.

3c. Synthesis of Ala-Thr-Arg-B(1–27)-Lys, Ser-Asp-Asp-Ala-Arg-A(1–21) insulin.

To the 280 ml of solution containing 118 mg of the single-chain precursor, obtained as described above, were added 3 ml of immobilized *A. lyticus* protease gel (see PCT/DK94/00347, page 45). After gentle stirring for 24 hours at 30° C. the gel was removed by filtration. The pH value was adjusted to 3.5 and the solution was filtered though a Milipore® 0.45µ filter. The double-chain, extended insulin was purified in 2 runs by RP-HPLC using a 2×20 cm column packed with 15µ spherical C18 silica of 100 Å pore size and 0.2 M Na$_2$SO$_4$, 0.04 M H$_3$PO$_4$, pH 3.5 as buffer, and using a gradient from 23 to 33% acetonitrile at a rate of 4 ml/min and a column temperature of 40° C. The double-chain, extended insulin eluted at about 30–31% acetonitrile. The acetonitrile was removed from the combined pools of 70 ml by evaporation in vacuo, and salts were removed by gelfiltration using a 5×47 cm column of Sephadex G-25 in 0.5 M acetic acid. The double-chain, extended insulin was isolated by lyophilization. Yield: 110 mg.

3d. Synthesis of $N^{\alpha A-5}, N^{\alpha B-3}, N^{\epsilon B28}$-tris(tetradecanoyl) Ala-Thr-Arg-B(1–27)-Lys, Ser-Asp-Asp-Ala-Arg-A(1–21) insulin.

110 mg of the double-chain, extended insulin obtained as described above were dissolved in a mixture of 0.84 ml of DMSO and 0.275 ml of 2 M diisopropylethylamine in NMP. The solution was cooled to 15° C. and 0.185 ml of 0.3 M tetradecanoic acid N-hydroxysuccinimide ester in DMSO/NMP (1:1, v/v) was added. After 2 hour at 15° C., the reaction was stopped by addition of 32.5 ml of 0.01 M glycine buffer in ethanol/water (60:40, v/v) and the pH value adjusted to 10.0. The triacylated intermediate was not isolated.

3e. Synthesis of $Lys^{B28}(N^{\epsilon}$-tetradecanoyl) des(B29–B30) human insulin.

To the resulting solution from the previous step was added 1.5 ml of immobilized trypsin gel (see PCT/DK94/00347, page 46). After gentle stirring at 15° C. for 18 hours, the gel was removed by filtration, the pH value adjusted to 9.0 and the solution applied to a 1.5×21 cm column of QAE-Sephadex® A-25. Isocratic elution was performed at a rate of 10 ml/h using a 0.12 M $NH_4Cl$ buffer in ethanol/water (60:40, v/v) adjusted to pH 9.0 with $NH_3$. The title compound emerged from the column after 250–390 ml, peaking at 330 ml. Finally, the buffer was changed to 0.01 M $NH_4HCO_3$ by gel filtration using Sephadex® G-50 Fine, and the product was isolated in the dry state by lyophilization. Yield: 47 mg.

Molecular mass of the title compound, found by MS: 5820±2, theory: 5819.

Molecular mass of the B-chain, found by MS: 3444±4, theory: 3442.

Molecular mass of the C-terminal fragment of B-chain digested by V8 protease, found by MS: 1128±2, theory: 1128.

Relative lipophilicity, $k'_{rel}$=121.

Disappearance half-life, $T_{50\%}$, after subcutaneous injection in pigs: 19.6±3.6 h (n=4).

Example 4

Synthesis of $Lys^{B27}(N^{\epsilon}$-tetradecanoyl) des(B28–B30) human insulin.

4a. Synthesis of Glu-Glu-Ala-Glu-Ala-Glu-Ala-Glu-Pro-Lys-Ala-Thr-Arg-B(1–26)-Lys-Ser-Asp-Asp-Ala-Arg-A(1–21) insulin precursor (SEQ ID NO:6-B(1–26)-SEQ ID NO:8-A(1–21)) from yeast strain yJB174 using the *S. cerevisiae* MF alpha prepro-leader.

The following oligonucleotides were synthesised:

```
                                          (SEQ ID NO:15)
#628   5-'CACTTGGTTGAAGCTTTGTACTTGGTTTGCGGTGAAAGAGG

TTTCTTCTACAAGTCTGACGATGCTAG-3'
```

```
                                          (SEQ ID NO:12)
#2371  5'-TTAATCTTAGTTTCTAGAGCCTGCGGG-3'
```

The DNA encoding Glu-Glu-Ala-Glu-Ala-Glu-Ala-Glu-Pro-Lys-Ala-Thr-Arg-B(1–26)-Lys-Ser-Asp-Asp-Ala-Arg-A(1–21) (SEQ ID NO:6-B(1–26)-SEQ ID NO:8- A(1–21)) was constructed in the same manner as described in Example 2 by substituting oligonucleotide #3881 with oligonucleotide #628.

The resulting plasmid was designated pJB174 and the yeast strain expressing Glu-Glu-Ala-Glu-Ala-Glu-Ala-Glu-Pro-Lys-Ala-Thr-Arg-B(1–26)-Lys-Ser-Asp-Asp-Ala-Arg-A(1–21) (SEQ ID NO:6- B(1–26)-SEQ ID NO:8-A(1–21)) was designated yJB174.

4b. Isolation of Glu-Glu-Ala-Glu-Ala-Glu-Ala-Glu-Pro-Lys-Ala-Thr-Arg-B(1–26)-Lys-Ser-Asp-Asp-Ala-Arg-A (1–21) insulin precursor.

The yJB174 strain was fermented for 72 hours and 3.5 liters of broth were collected. Yeast cells were removed by centrifugation, the pH value was adjusted to 3.0 using sulphuric acid and the solution was diluted with water to 8 liters in order to decrease the salt concentration. The resulting conductivity was 7.9 mS/cm. The insulin precursor was concentrated using a Pharmacia Streamline® 50 column packed with 300 ml of Streamline® SP ion exchanger. After wash with 25 mM citrate buffer, pH 3.6, the precursor was eluted by 0.5 M $NH_3$ and the fraction from 300 to 600 ml was collected. Free ammonia was evaporated in vacuo at room temperature and the pH value of the resulting 280 ml was adjusted to 9.0 with hydrochloric acid.

4c. Synthesis of Ala-Thr-Arg-B(1–26)-Lys, Ser-Asp-Asp-Ala-Arg-A(1–21) insulin.

To the 280 ml of solution of the single-chain precursor obtained as described above was added 3 ml of immobilized *A. lyticus* protease gel (see PCT/DK94/00347, page 45). After gentle stirring for 13 hours at 30° C. the gel was removed by filtration. The pH value was adjusted to 2.5 and the solution was filtered though a Milipore® 0.45µ filter. The double-chain, extended insulin was purified in 4 runs by RP-HPLC using a 2×20 cm column packed with 15µ spherical C18 silica of 100 Å pore size and 0.2 M $Na_2SO_4$, 0.04 M $H_3PO_4$, pH 2.5 as buffer, and using a gradient from 24 to 33% acetonitrile. The double-chain, extended insulin eluted at about 30–31% acetonitrile. The acetonitrile was removed from the combined pools by evaporation in vacuo, and the salts were removed by gelfiltration using a 5×47 cm column of Sephadex G-25 in 0.5 M acetic acid. The double-chain, extended insulin was isolated by lyophilization. Yield: 69 mg.

4d. Synthesis of $N^{\alpha A-5}, N^{\alpha B-3}, N^{\epsilon B27}$-tris(tetradecanoyl) Ala-Thr-Arg-B(1–26)-Lys, Ser-Asp-Asp-Ala-Arg-A(1–21) insulin.

62 mg of the double-chain, extended insulin obtained as described under 4e was dissolved in a mixture of 0.44 ml of DMSO and 0.15 ml of 2 M diisopropylethylamine in NMP. The solution was cooled to 15° C. and 0.096 ml of 0.3 M tetradecanoic acid N-hydroxysuccinimide ester in DMSO/NMP (1:1, v/v) was added. After 2 hours at 15° C. the reaction was stopped by addition of 17 ml of 0.01 M glycine buffer in ethanol/water (60:40, v/v) and the pH value adjusted to 10.0. The triacylated intermediate was not isolated.

4e. Synthesis of $Lys^{B27}(N^{\epsilon}$-tetradecanoyl) des(B28–B30) human insulin.

To the solution from the previous step was added 1 ml of immobilized trypsin gel (see PCT/DK94/00347, page 46). After gentle stirring at 15° C. for 26 hours, the gel was removed by filtration, the pH value adjusted to 9.0 and the solution applied to a 1.5×25.5 cm column of QAE-Sephadex® A-25. Isocratic elution was performed at a rate of 17.3 ml/h using a 0.12 M $NH_4Cl$ buffer in ethanol/water (60:40, v/v) adjusted to pH 9.0 with $NH_3$. The title compound emerged from the column after 360 ml, and a pool from 272 to 455 ml was collected. Finally, the buffer was changed to 0.01 M $NH_4HCO_3$ by gel filtration on Sephadex® G-50 Fine, and the product isolated in the dry state by lyophilization. Yield: 38 mg.

Molecular mass of the title compound, found by MS: 5720±6, theory: 5718.

Molecular mass of the B-chain, found by MS: 3342±4, theory: 3340.

Molecular mass of the C-terminal fragment of B-chain digested by V8 protease, found by MS: 1027±2, theory: 1027.

Relative lipophilicity, $k'_{rel}$=151.

Disappearance half-life, $T_{50\%}$, after subcutaneous injection in pigs: 15.2±2.2 h (n=5).

Example 5

Synthesis of $Lys^{B26}(N^\epsilon$-tetradecanoyl) des(B27–B30) human insulin.

5a. Synthesis of Glu-Glu-Ala-Glu-Ala-Glu-Ala-Glu-Pro-Lys-Ala-Thr-Arg-B(1–25)-Lys-Ser-Asp-Asp-Ala-Arg-A (1–21) insulin precursor (SEQ ID NO:6-B(1–26)-SEQ ID NO:8- A(1–21)) from yeast strain yJB175 using the *S. cerevisiae* MF alpha prepro-leader.

The following oligonucleotides were synthesised:

```
                                    (SEQ ID NO:16)
#629  5'-CACTTGGTTGAAGCTTTGTACTTGGTTTGCGGTGAAAGAGG
    TTTCTTCAAAGTCTGACGATGCTAG-3'

(SEQ ID NO:12)
2371 5'-TTAATCTTAGTTTCTAGAGCCTGCGGG-3'
```

The DNA encoding Glu-Glu-Ala-Glu-Ala-Glu-Ala-Glu-Pro-Lys-Ala-Thr-Arg-B(1–25)-Lys-Ser-Asp-Asp-Ala-Arg-A(1–21) (SEQ ID NO:6-B(1–26)-SEQ ID NO:8-A(1–21)) was constructed in the same manner as described in Example 2 by substituting oligonucleotide #3881 with oligonucleotide #629.

The resulting plasmid was designated pJB175 and the yeast strain expressing Glu-Glu-Ala-Glu-Ala-Glu-Ala-Glu-Pro-Lys-Ala-Thr-Arg-B(1–25)-Lys-Ser-Asp-Asp-Ala-Arg-A(1–21) (SEQ ID NO:6-B(1–26)-SEQ ID NO:8-A(1–21)) was designated yJB175.

5b. Isolation of Glu-Glu-Ala-Glu-Ala-Glu-Ala-Glu-Pro-Lys-Ala-Thr-Arg-B(1–25)-Lys-Ser-Asp-Asp-Ala-Arg-A (1–2 1) insulin precursor.

The yJB175 strain was fermented for 72 hours and 3.7 liters of broth were collected. Yeast cells were removed by centrifugation, the pH value was adjusted to 3.0 using sulphuric acid and the solution was diluted with water to 8.5 liters in order to decrease the salt concentration. The resulting conductivity was 7.7 mS/cm. The insulin precursor was concentrated using a Pharmacia Strealine® 50 column packed with 300 ml of Streamline® SP ion exchanger. After wash with 25 mM citrate buffer, pH 3.6, the precursor was eluted by 0.5 M ammonia and the fraction from 300 to 600 ml was collected. Free ammonia was evaporated in vacuo at room temperature and the pH value of the resulting 270 ml of solution was adjusted to 9.0 with hydrochloric acid.

5c. Synthesis of Ala-Thr-Arg-B(1–25)-Lys, Ser-Asp-Asp-Ala-Arg-A(1–21) insulin.

To the 270 ml solution of the single-chain precursor obtained as described above was added 3 ml of immobilized *A. lyticus* protease gel (see PCT/DK94/00347, page 45). After gentle stirring for 23 hours at 30° C., the gel was removed by filtration. The pH value was adjusted to 2.5 and the solution was filtered though a Milipore® 0.45μ filter. The double-chain, extended insulin was purified in 4 runs by RP-HPLC using a 2×20 cm column packed with 15μ spherical C18 silica of 100 Å pore size and 0.2 M $Na_2SO_4$, 0.04 M $H_3PO_4$, pH 3.5 as buffer, and using a gradient from 24 to 33% acetonitrile. The double-chain, extended insulin eluted at about 29–31% acetonitrile. The acetonitrile was removed from the combined pools by evaporation in vacuo, and the salts were removed by gelfiltration using a 5×47 cm column of Sephadex® G-25 in 0.5 M acetic acid. The double-chain, extended insulin was isolated by lyophilization. Yield: 81 mg.

5d. Synthesis of $N^{\alpha A-5},N^{\alpha B-3},N^{\epsilon B26}$-tris(tetradecanoyl) Ala-Thr-Arg-B(1–25)-Lys, Ser-Asp-Asp-Ala-Arg-A(1–21) insulin.

80 mg of the double-chain, extended insulin was dissolved in a mixture of 0.56 ml of DMSO and 0.19 ml of 2 M diisopropylethylamine in NMP. The solution was cooled to 15° C. and 0.124 ml of 0.3 M tetradecanoic acid N-hydroxysuccinimide ester in DMSO/NMP (1:1, v/v) was added. After 2 hour at 15 ° C. the reaction was stopped by addition of 21.8 ml of 0.01 M glycine buffer in ethanol/water (60:40, v/v) and the pH value adjusted to 10.0. The triacylated intermediate was not isolated.

5e. Synthesis of $LyS^{B26}(N^\epsilon$-tetradecanoyl) des (B27–B30), human insulin.

To the solution from the previous step was added 1 ml of immobilized trypsin gel (see PCT/DK94/00347, page 46). After gentle stirring at 15° C. for 23 hours the gel was removed by filtration, the pH value was adjusted to 9.0 and the solution applied to a 1.5×25.5 cm column of QAE-Sephadex® A-25. Isocratic elution was performed at a rate of 19.3 ml/h using a 0.12 M $NH_4Cl$ buffer in ethanol/water (60:40, v/v) adjusted to pH 9.0 with ammonia. The title compound emerged from the column after 320 ml, and a fraction from 320 to 535 ml was collected. Finally, the buffer was changed to 0.01 M $NH_4HCO_3$ by gel filtration on Sephadex® G-50 Fine, and the product isolated in the dry state by lyophilization. Yield: 25 mg.

Molecular mass of the title compound found by MS. 5555±6, theory: 5555.

Molecular mass of the B-chain found by MS: 3179±4, theory: 3178.

Molecular mass of the C-terminal fragment of B-chain digested by V8 protease found by MS: 864±1, theory: 863.5.

Relative lipophilicity, $k'_{rel}$=151.

Disappearance half-life, $T_{50\%}$, after subcutaneous injection in pigs: 14.4±1.5 h (n=5).

Example 6

Synthesis of (N(1-carboxytridecyl)-2-amidosuccinyl)-Phe$^{\alpha B1}$ des(B30) human insulin.

A1,B29-diBoc-des(B30) human insulin (200 mg, 0.033 mmol) was dissolved in DMF (15 ml) and triethylamine (20 µl) was added. N(1-carbomethoxytridecyl)-2-amidosuccinic acid N-hydroxysuccinimide ester (16 mg, 0.033 mmol) was added and after 4 hours at room temperature the reaction mixture was evaporated in vacuo to dryness. The Boc groups were removed by treatment for 30 min at room temperature with trifluoroacetic acid (5 ml). The trifluoroacetic acid was removed by evaporation in vacuo. The residue was dissolved at 0° C. in 0.1 N NaOH (20 ml). The saponification of the methyl ester was accomplished after 1 hour at 0° C. The pH value of the reaction mixture was adjusted to 5.0 by acetic acid and ethanol (5 ml) was added. The precipitate formed was isolated by centrifugation. The title compound was purified from the precipitate by ion exchange chromatography using a 2.5×27 cm column of QAE-Sephadex® A25.

The precipitate was dissolved ethanol/water (60:40, v/v) (25 ml) by adjustment of the pH value to 9.8 using ammonia and the solution was applied to the column. Elution was carried out in NH$_3$/NH$_4$Cl buffers at pH 9.0, using a linear gradient from 0.12 to 0.18 M NH$_4$Cl in ethanol/water (60:40, v/v) and a total of 1000 ml of eluent. The UV absorbance of the eluate was monitored at 280 nm and fractions of 10 ml were collected. The title compound emerged from the column in fractions 62 to 72. The title compound was precipitated by diluting the pool with 2 volumes of water and adjusting the pH value to 5.0. After centrifugation the precipitate was washed with water and after a second centrifugation the product was dried in vacuo. Yield: 10 mg.

Molecular weight, found by PDMS: 6032, theory: 6032.

Relative lipophilicity, k'$_{rel}$=140.

Disappearance half-life, T$_{50\%}$, after subcutaneous injection in pigs: 8.65±11.65 hours (n=5).

Example 7

Phe$^{\alpha B1}$-tetradecanoyl-glutamyl-glycyl des(B30) human insulin.

A1,B29-diBoc des(B30) human insulin (200 mg, 0.033 mmol) was dissolved in DMF (15 ml) and triethylamine (100 µl) was added. Myristoyl-Glu(γ-OtBu)-Gly N-hydroxysuccinimide ester (95 mg, 0.17 mmol) was added and after 4 hours at room temperature the reaction mixture was evaporated to dryness in vacuo. The Boc and tBu groups were removed by treatment for 30 min at room temperature with trifluoroacetic acid (5 ml). The trifluoroacetic acid was removed by evaporation in vacuo.

The title compound was purified from the precipitate by RP-HPLC using a C18 silica column and eluting with a linear gradient from 16 to 64% acetonitrile in a 50 mM Tris/phosphate buffer containing 75 mM (NH$_4$)$_2$SO$_4$ at pH 7. The title compound emerged from the column at about 50% acetonitrile. The acetonitrile was evaporated in vacuo, and ethanol was added to 20% (v/v). Adjustment of the pH value to 5.0 caused the product to precipitate. After centrifugation the precipitate was dissolved in 10 mM NH$_4$HCO$_3$, desalted by gel filtration using Sephadex G-25 and lyophilized. Yield: 97 mg.

Molecular mass, found by PDMS: 6105, theory: 6104.

Example 8

Synthesis of Gly$^{B28}$,Thr$^{B29}$,Lys$^{B30}$(N$^\epsilon$-tetradecanoyl) Human insulin 8a. Synthesis of Glu-Glu-Ala-Glu-Ala-Glu-Ala-Glu-Pro-Lys-Ala-Thr-Arg-B(1–27)-Gly-Thr-Lys-Ser-Asp-Asp-Ala-Arg-A(1–21) insulin precursor from yeast strain yKV195 using the *S. cerevisiae* MF alpha prepro-leader.

The following oligonucleotides were synthesised:

```
#4790  5'-TTGGTTGAAGCTTTGTACTTGGTTTGCGGTGAAAGAGGTT

TCTTCTACACTGGTACCAAGTCTGACGATGCTAGAGGTATTGT

CG-3'

#2371  5'-TTAATCTTAGTTTCTAGAGCCTGCGGG-3'
```

The DNA encoding Glu-Glu-Ala-Glu-Ala-Glu-Ala-Glu-Pro-Lys-Ala-Thr-Arg-B(1–27)-Gly-Thr-Lys-Ser-Asp-Asp-Ala-Arg-A(1–21) was constructed in the same manner as described in Example 2 by substituting oligonucleotide #3881 with oligonucleotide #4790.

The resulting plasmid was designated pKV195 and the yeast strain expressing Glu-Glu-Ala-Glu-Ala-Glu-Ala-Glu-Pro-Lys-Ala-Thr-Arg-B(1–27)-Gly-Thr-Lys-Ser-Asp-Asp-Ala-Arg-A(1–21) was designated yKV195.

8b. Isolation of Glu-Glu-Ala-Glu-Ala-Glu-Ala-Glu-Pro-Lys-Ala-Thr-Arg-B(1–27)-Gly-Thr-Lys-Ser-Asp-Asp-Ala-Arg-A(1–21) insulin precursor.

The yKV195 strain was fermented for 72 hours and 4.4 liters of broth were collected. Yeast cells were removed by centrifugation, the pH value was adjusted to 3.0 using sulphuric acid and 3.6 liters of water were added to dilute salts to a conductivity of 7.7 mS/cm. The insulin precursor was concentrated using a Pharmacia Strealine® 50 column packed with 300 ml of Streamline® SP ion exchanger. After wash with 3 liters of 25 mM citrate buffer, pH 3.6, the precursor was eluted using 0.5 M ammonia and the fraction from 300 to 600 ml was collected. Free ammonia was evaporated in vacuo at room temperature and the pH value of the resulting 280 ml was adjusted to 9.0 with hydrochloric acid.

8c. Synthesis of Ala-Thr-Arg-B(1–27)-Gly-Thr-Lys, Ser-Asp-Asp-Ala-Arg-A(1–21) insulin.

To the 280 ml of solution containing 300 mg of the single-chain precursor were added 3 ml of immobilized *A. lyticus* protease gel (see PCT/DK94/00347, page 45). After gentle stirring for 17 hours at 30° C. the gel was removed by filtration. The pH value was adjusted to 3.5 and the solution was filtered though a Milipore® 0.45µ filter. The double-chain, extended insulin was purified in 3 runs by RP-HPLC using a 2×20 cm column packed with 10µ spherical C18 silica of 120 Å pore size and 0.2 M Na$_2$SO$_4$, 0.04 M H$_3$PO$_4$, pH 3.5 as buffer, and using a gradient from 23 to 33% acetonitrile at a rate of 4 ml/min and a column temperature of 40° C. The double-chain, extended insulin eluted at about 30–31% acetonitrile. The acetonitrile was removed from the combined pools of 70 ml by evaporation in vacuo, and the salt were removed by gelfiltration using a 5×47 cm column of Sephadex® G-25 and 0.5 M acetic acid. The double-chain, extended insulin was isolated by lyophilization. Yield: 176 mg.

8d. Synthesis of $N^{\alpha A-5},N^{\alpha B-3},N^{\epsilon B30}$-tris(tetradecanoyl) Ala-Thr-Arg-B(1–27)-Gly-Thr-Lys, Ser-Asp-Asp-Ala-Arg-A(1–21) insulin.

176 mg of the double-chain, extended insulin was dissolved in a mixture of 1.4 ml of DMSO and 0.275 ml of 2 M diisopropylethylamine in NMP. The solution was cooled to 15° C. and 0.963 ml of 0.3 M tetradecanoic acid N-hydroxysuccinimide ester in DMSO/NMP (1:1, v/v) was added. After 20 hour at 15° C. the reaction was stopped by addition of 50 ml of 0.01 M glycine buffer in ethanol/water (60:40, v/v) and the pH value adjusted to 10.0. The triacylated intermediate was not isolated.

8e. Synthesis of $Gly^{B28},Thr^{B29},Lys^{B30}(N^{\epsilon}$-tetradecanoyl) human insulin.

To the solution from the previous step was added 2.5 ml of immobilized trypsin gel (see PCT/DK94/00347, page 46). After gentle stirring at 15° C. for 5 hours, the gel was removed by filtration; the pH value adjusted to 9.0 and the solution applied to a 1.5×26.5 cm column of QAE-Sephadex® A-25. Isocratic elution was performed at a rate of 9.3 ml/h using a 0.12 M $NH_4Cl$ buffer in ethanol/water (60:40, v/v) adjusted to pH 9.0 with ammonia. The title compound emerged from the column after 325–455 ml, peaking at 380 ml. Finally, the buffer was changed to 0.01 M $NH_4HCO_3$ by gel filtration using Sephadex® G-50 Fine, and the product isolated in the dry state by lyophilization. Yield: 50 mg.

Molecular mass of the title compound, found by MS: 5979±6, theory: 5977.

Molecular mass of the B-chain, found by MS: 3600±4, theory: 3600.

Molecular mass of the C-terminal fragment of B-chain digested by V8 protease, found by MS: 1286±2, theory: 1286.

Relative lipophilicity, $k'_{rel}$=103.

Disappearance half-life, $T_{50\%}$, after subcutaneous injection in pigs: 17±2 h (n=4).

Example 9

Synthesis of $Gly^{B28},Lys^{B29}(N^{\epsilon}$-tetradecanoyl) human insulin.

9a. Synthesis of Glu-Glu-Ala-Glu-Ala-Glu-Ala-Glu-Pro-Lys-Ala-Thr-Arg-B(1–27)-Gly-Lys-Ser-Asp-Asp-Ala-Arg-A(1–21) insulin precursor from yeast strain yKV196 using the *S. cerevisiae* MF alpha prepro-leader.

The following oligonucleotides were synthesised:

```
#4791  5'-TTGGTTGAAGCTTTGTACTTGGTTTGCGGTGAAAGAGGTTT
           CTTCTACACCGGTAAGTCTGACGATGCTAGAGGTATTGTCG-3'
#2371  5'-TTAATCTTAGTTTCTAGAGCCTGCGGG-3'
```

The DNA encoding Glu-Glu-Ala-Glu-Ala-Glu-Ala-Glu-Pro-Lys-Ala-Thr-Arg-B(1–27)-Gly-Lys-Ser-Asp-Asp-Ala-Arg-A(1–21) was constructed in the same manner as described in Example 2 by substituting oligonucleotide #3881 with oligonucleotide #4791.

The resulting plasmid was designated pKV196 and the yeast strain expressing Glu-Glu-Ala-Glu-Ala-Glu-Ala-Glu-Pro-Lys-Ala-Thr-Arg-B(1–27)-Gly-Lys-Ser-Asp-Asp-Ala-Arg-A(1–21) was designated yKV196.

9b. Isolation of Glu-Glu-Ala-Glu-Ala-Glu-Ala-Glu-Pro-Lys-Ala-Thr-Arg-B(1–27)-Gly-Lys-Ser-Asp-Asp-Ala-Arg-A(1–21) insulin precursor.

The yKV196 strain was fermented for 72 hours and 3.6 liters of broth were collected. Yeast cells were removed by centrifugation, the pH value was adjusted to 3.0 using sulphuric acid and 3.4 liters of water were added to dilute salts to a conductivity of 7.7 mS/cm. The insulin precursor was concentrated to 300 ml using the procedure described in Example 8b.

9c. Synthesis of Ala-Thr-Arg-B(1–27)-Gly-Lys, Ser-Asp-Asp-Ala-Arg-A(1–21) insulin.

To the 300 ml solution at pH 9.0 containing 390 mg of the single-chain precursor were added 5 ml of immobilized *A. lyticus* protease gel (see PCT/DK94/00347, page 45). After gentle stirring for 40 hours at 30° C., the gel was removed by filtration. The pH value was adjusted to 3.5 and the solution was filtered though a Milipore® 0.45µ filter. The double-chain, extended insulin was purified in 3 runs by RP-HPLC using a 2×20 cm column packed with 10µ spherical C18 silica of 120 Å pore size and 0.2 M $Na_2SO_4$, 0.04 M $H_3PO_4$, pH 3.5 as buffer, and using a gradient from 23 to 33% acetonitrile at a rate of 4 ml/min and a column temperature of 40° C. The double-chain, extended insulin eluted at about 29% acetonitrile. The acetonitrile was removed from the combined pools of 60 ml by evaporation in vacuo, and the salt were removed by gelfiltration using a 5×47 cm column of Sephadex® G-25 and 0.5 M acetic acid. The double-chain, extended insulin was isolated by lyophilization. Yield: 154 mg.

9d. Synthesis of $N^{\alpha A-5},N^{\alpha B-3},N^{\epsilon B29}$-tris(tetradecanoyl) Ala-Thr-Arg-B(1–27)-Gly-Lys, Ser-Asp-Asp-Ala-Arg-A (1–21) insulin.

154 mg of the double-chain, extended insulin was dissolved in a mixture of 1.05 ml of DMSO and 0.329 ml of 2 M diisopropylethylamine in NMP. The solution was cooled to 15° C. and 0.22 ml of 0.3 M tetradecanoic acid N-hydroxysuccinimide ester in DMSO/NMP (1:1, v/v) was added. After 2 hour at 15° C., the reaction was stopped by addition of 40 ml of 0.01 M glycine buffer in ethanol/water (60:40, v/v) and the pH value adjusted to 10.0. The triacylated intermediate was not isolated.

9e. Synthesis of $Gly^{B28},Lys^{B29}(N^{\epsilon}$-tetradecanoyl) human insulin.

To the solution from the previous step was added 1.5 ml of immobilized trypsin gel (see PCT/DK94/00347, page 46). After gentle stirring at 15° C. for 21 hours, the gel was removed by filtration, the pH value adjusted to 9.0 and the product in 43 ml solution was applied to a 1.5×26.0 cm column of QAE-Sephadex® A-25. Isocratic elution was performed at a rate of 9:5 ml/h using a 0.12 M $NH_4Cl$ buffer in ethanol/water (60:40, v/v) adjusted to pH 9.0 with ammonia. The title compound emerged from the column after 190–247 ml, is peaking at 237 ml. Finally, the buffer was changed to 0.01 M $NH_4HCO_3$ by gel filtration using Sephadex® G-50 Fine, and the product isolated in the dry state by lyophilization. Yield: 67 mg.

Molecular mass of the title compound, found by MS: 5877±2, theory: 5876.

Molecular mass of the B-chain, found by MS: 3499±3, theory: 3499.

Molecular mass of the C-terminal fragment of B-chain digested by V8 protease, found by MS: 1184±2, theory: 1185.

Relative lipophilicity, $k'_{rel}$=118.5.

Disappearance half-life, $T_{50\%}$, after subcutaneous injection in pigs: 25±9 h (n=4).

What is claimed is:

1. A pharmaceutical composition for the treatment of diabetes in a patient in need of such treatment, comprising a sodium phosphate buffer and a therapeutically effective amount of an insulin derivative having the following sequence:

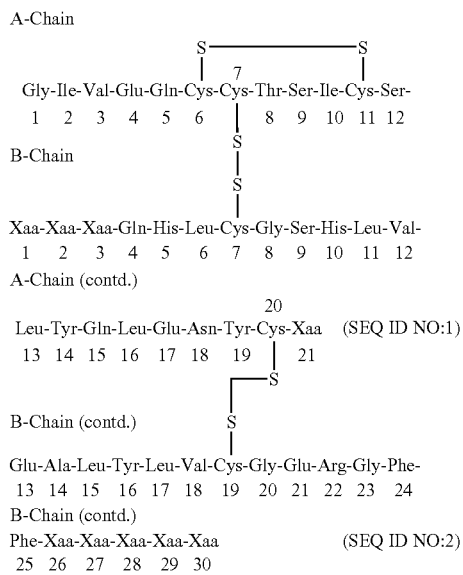

wherein
Xaa at position A21 is any codable amino acid except Lys, Arg and Cys;
Xaa at positions B1, B2, B3, B26, B27, B28, B29 and B30 are, independent of each other, any codable amino acid except Cys or deleted; and a lipophilic group W is attached to the amino group of the N-terminal amino acid of the B-chain in which the lipophilic group W has from 12 to 40 carbon atoms and optionally contains a group which can be negatively charged or a lipophilic group Z is attached to the carboxyl group of the C-terminal amino acid of the B-chain in which the lipophilic group Z has from 12 to 40 carbon atoms and optionally contains a group which can be negatively charged, provided that:
(a) when B1-B2-B3 is Phe-Val-Asn and A21 is Asn and B26-B27-B28-B29-B30 is Tyr-Thr-Pro-Lys-Thr or Tyr-Thr-Pro-Lys-Ala, then the lipophilic group W or Z always contains a group which can be negatively charged; and
(b) when B29 and B30 are deleted and the lipophilic group Z is present and B1, B2 and B3 are not deleted then B1-B2 is different from Phe-Val or B26-B27-B28 is different from Tyr-Thr-Pro or both B1-B2 and B26-B27-B28 are different from said sequences; and
(c) when B29 and B30 are deleted and the lipophilic group Z is present and one of B1, B2 or B3 is deleted then the N-terminal amino acid of the B-chain is different from Val or the sequence B26-B27-B28 is different from Tyr-Thr-Pro or both the N-terminal amino acid of the B-chain and the sequence B26-B27-B28 are different from Val and Tyr-Thr-Pro respectively.

2. A method of treating diabetes in a patient in need of such a treatment, comprising administering to the patient a therapeutically effective amount of the pharmaceutical composition of claim 1.

3. A pharmaceutical composition for the treatment of diabetes in a patient in need of such treatment, comprising a therapeutically effective amount of a hexameric insulin complex that comprises at least one insulin derivative having the following sequence:

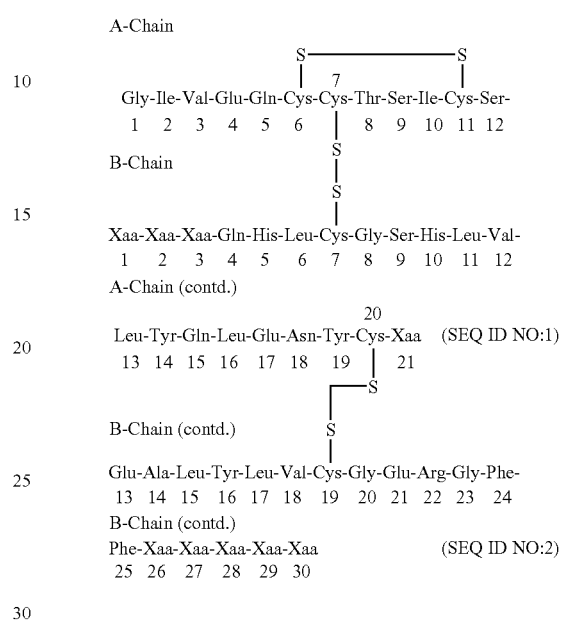

wherein
Xaa at position A21 is any codable amino acid except Lys, Arg and Cys;
Xaa at positions B1, B2, B3, B26, B27, B28, B29 and B30 are, independent of each other, any codable amino acid except Cys or deleted; and a lipophilic group W is attached to the amino group of the N-terminal amino acid of the B-chain in which the lipophilic group W has from 12 to 40 carbon atoms and optionally contains a group which can be negatively charged or a lipophilic group Z is attached to the carboxyl group of the C-terminal amino acid of the B-chain in which the lipophilic group Z has from 12 to 40 carbon atoms and optionally contains a group which can be negatively charged, provided that
(a) when B1-B2-B3 is Phe-Val-Asn and A21 is Asn and B26-B27-B28-B29-B30 is Tyr-Thr-Pro-Lys-Thr or Tyr-Thr-Pro-Lys-Ala, then the lipophilic group W or Z always contains a group which can be negatively charged; and
(b) when B29 and B30 are deleted and the lipophilic group Z is present and B1, B2 and B3 are not deleted then B1-B2 is different from Phe-Val or B26-B27-B28 is different from Tyr-Thr-Pro or both B1-B2 and B26-B27-B28 are different from said sequences; and
(c) when B29 and B30 are deleted and the lipophilic group Z is present and one of B1, B2 or B3 is deleted then the N-terminal amino acid of the B-chain is different from Val or the sequence B26-B27-B28 is different from Tyr-Thr-Pro or both the N-terminal amino acid of the B-chain and the sequence B26-B27-B28 are different from Val and Tyr-Thr-Pro respectively.

4. A method of treating diabetes in a patient in need of such a treatment, comprising administering to the patient a therapeutically effective amount of the pharmaceutical composition of claim 3.

5. An insulin derivative having the following sequence:

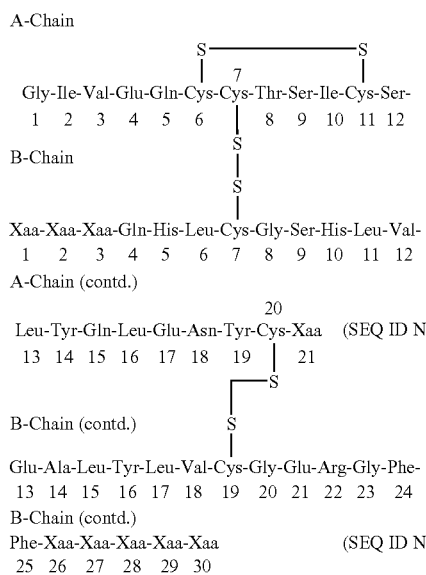

A-Chain
```
         S─────────S
         │    7    │
Gly-Ile-Val-Glu-Gln-Cys-Cys-Thr-Ser-Ile-Cys-Ser-
 1   2   3   4   5   6    │   8   9  10  11  12
                          S
B-Chain                   │
                          S
                          │
Xaa-Xaa-Xaa-Gln-His-Leu-Cys-Gly-Ser-His-Leu-Val-
 1   2   3   4   5   6   7   8   9  10  11  12
```
A-Chain (contd.)
```
                              20
Leu-Tyr-Gln-Leu-Glu-Asn-Tyr-Cys-Xaa    (SEQ ID NO:1)
 13  14  15  16  17  18  19  │  21
                            ┌─S
B-Chain (contd.)            S
                            │
Glu-Ala-Leu-Tyr-Leu-Val-Cys-Gly-Glu-Arg-Gly-Phe-
 13  14  15  16  17  18  19  20  21  22  23  24
```
B-Chain (contd.)
Phe-Xaa-Xaa-Xaa-Xaa-Xaa        (SEQ ID NO:2)
 25  26  27  28  29  30 wherein

Xaa at position A21 is any codable amino acid except Lys, Arg and Cys;

Xaa at positions B1, B2 and B3 are independently any codable amino acid except Cys or deleted;

Xaa at positions B26, B27, B28 and B29 are independently any codable amino acid except Cys;

Xaa at position B30 is a dipeptide which does not contain Cys or Arg, a tripeptide which does not contain Cys or Arg, or a tetrapeptide which does not contain Cys or Arg; and (a) a lipophilic group W is attached to the amino group of the N-terminal amino acid of the B-chain in which the lipophilic group W has from 12 to 40 carbon atoms and optionally contains a group which can be negatively charged or (b) a lipophilic group Z is attached to the carboxyl group of the C-terminal amino acid of the B-chain in which the lipophilic group Z has from 12 to 40 carbon atoms and optionally contains a group which can be negatively charged.

6. A pharmaceutical composition comprising a therapeutically effective amount of the derivative of claim 5 together with a pharmaceutically acceptable carrier.

7. A method of treating diabetes in a patient in need of such a treatment, comprising administering to the patient a pharmaceutical composition of claim 6.

8. An insulin derivative having the following sequence:

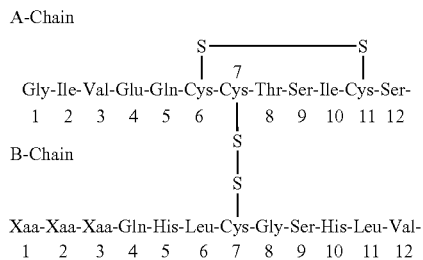

A-Chain
```
         S─────────S
         │    7    │
Gly-Ile-Val-Glu-Gln-Cys-Cys-Thr-Ser-Ile-Cys-Ser-
 1   2   3   4   5   6    │   8   9  10  11  12
                          S
B-Chain                   │
                          S
                          │
Xaa-Xaa-Xaa-Gln-His-Leu-Cys-Gly-Ser-His-Leu-Val-
 1   2   3   4   5   6   7   8   9  10  11  12
```

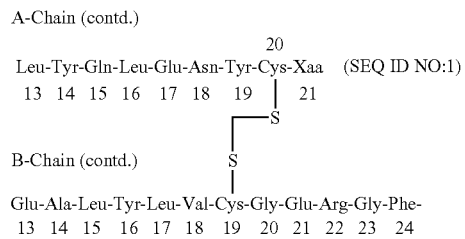

A-Chain (contd.)
```
                              20
Leu-Tyr-Gln-Leu-Glu-Asn-Tyr-Cys-Xaa    (SEQ ID NO:1)
 13  14  15  16  17  18  19  │  21
                            ┌─S
B-Chain (contd.)            S
                            │
Glu-Ala-Leu-Tyr-Leu-Val-Cys-Gly-Glu-Arg-Gly-Phe-
 13  14  15  16  17  18  19  20  21  22  23  24
```

B-Chain (contd.)
Phe-Xaa-Xaa-Xaa-Xaa-Xaa        (SEQ ID NO:2)
 25  26  27  28  29  30 wherein at least one amino acid or sequence of amino acids selected from the group comprising B1, B30, B(29–30), B(28–30), B(27–30) and B(26-30) is deleted and Xaa at position A21 is any codable amino acid except Lys, Arg and Cys;

Xaa at positions B1, B2, B3, B26, B27, B28 and B29 are independently any codable amino acid except Cys or deleted;

Xaa at position B30 is any codable amino acid except Cys, a dipeptide which does not contain Cys or Arg, a tripeptide which does not contain Cys or Arg, a tetrapeptide which does not contain Cys or Arg, or deleted; and (a) a lipophilic group W is attached to the amino group of the N-terminal amino acid of the B-chain in which the lipophilic group W has from 12 to 40 carbon atoms and optionally contains a group which can be negatively charged or (b) a lipophilic group Z is attached to the carboxyl group of the C-terminal amino acid of the B-chain in which the lipophilic group Z has from 12 to 40 carbon atoms and optionally contains a group which can be negatively charged, provided that:

(a) when B29 and B30 are deleted and a group Z as defined above is present at the C-terminal amino acid of the B-chain and neither B1, B2 nor B3 is deleted then B1-B2 is different from Phe-Val or B26-B27-B28 is different from Tyr-Thr-Pro or both B1-B2 and B26-B27-B28 are different from said sequences; and (b) when B29 and B30 are deleted and a group Z as defined above is present at the C-terminal amino acid of the B-chain and one of B 1, B2 or B3 is deleted then the N-terminal amino acid of the B-chain is different from Val or the sequence B26-B27-B28 is different from Tyr-Thi-Pro or both the N-terminal amino acid of the B-chain and the sequence B26-B27-B28 are different from Val and Tyr-Thr-Pro respectively.

9. A pharmaceutical composition, comprising a therapeutically effective amount of the derivative of claim 8 together with a pharmaceutically acceptable carrier.

10. A method of treating diabetes in a patient in need of such a treatment, comprising administering to the patient a pharmaceutical composition of claim 9.

11. An insulin derivative having the following sequence:

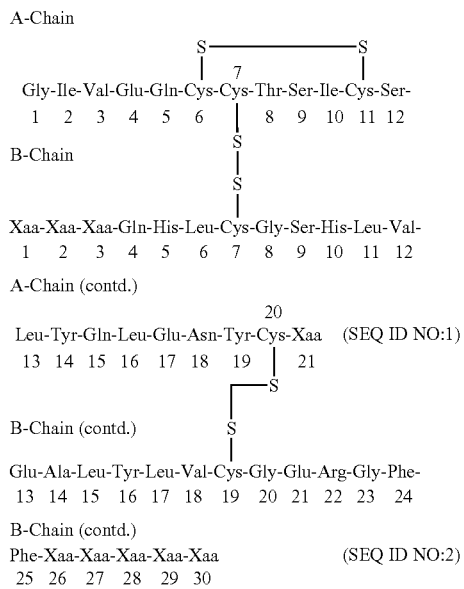

A-Chain (contd.)
Leu-Tyr-Gln-Leu-Glu-Asn-Tyr-Cys-Xaa    (SEQ ID NO:1)
13  14  15  16  17  18  19     21
                                    20

B-Chain (contd.)
Glu-Ala-Leu-Tyr-Leu-Val-Cys-Gly-Glu-Arg-Gly-Phe-
13  14  15  16  17  18  19  20  21  22  23  24

B-Chain (contd.)
Phe-Xaa-Xaa-Xaa-Xaa-Xaa    (SEQ ID NO:2)
25  26  27  28  29  30 wherein
 Xaa at position A21 is any codable amino acid except Lys, Arg and Cys;
 Xaa at positions B1, B2 and B3 are independently any codable amino acid except Cys or deleted;
 Xaa at positions B26, B27, B28 and B29 are independently any codable amino acid except Cys;
 Xaa at position B30 is Lys; and (a) a lipophilic group W is attached to the amino group of the N-terminal amino acid of the B-chain in which the lipophilic group W has from 12 to 40 carbon atoms and optionally contains a group which can be negatively charged or (b) a lipophilic group Z is attached to the carboxyl group of the C-terminal amino acid of the B-chain in which the lipophilic group Z has from 12 to 40 carbon atoms and optionally contains a group which can be negatively charged.

12. A pharmaceutical composition, comprising a therapeutically effective amount of the derivative of claim 11 together with a pharmaceutically acceptable carrier.

13. A method of treating diabetes in a patient in need of such a treatment, comprising administering to the patient the pharmaceutical composition of claim 12.

* * * * *

UNITED STATES PATENT AND TRADEMARK OFFICE
CERTIFICATE OF CORRECTION

PATENT NO. : 7,229,964 B2 Page 1 of 1
APPLICATION NO. : 10/620651
DATED : June 12, 2007
INVENTOR(S) : Markussen et al.

It is certified that error appears in the above-identified patent and that said Letters Patent is hereby corrected as shown below:

Column 40, Claim 8, Line 57: "Tyr-Thi-Pro" should read --Tyr-Thr-Pro--.

Signed and Sealed this

Thirty-first Day of March, 2009

JOHN DOLL
*Acting Director of the United States Patent and Trademark Office*

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
       (A) LENGTH: 21 amino acids
       (B) TYPE: amino acid
       (C) STRANDEDNESS: single
       (D) TOPOLOGY: linear (xi) SEQUENCE DESCRIPTION: SEQ ID NO: 1:

Gly Ile Val Glu Gln Cys Cys Thr Ser Ile Cys Ser Leu Tyr Gln Leu
1               5                  10                  15

Glu Asn Tyr Cys Xaa
            20

(2) INFORMATION FOR SEQ ID NO: 2:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 2:

Xaa Xaa Xaa Gln His Leu Cys Gly Ser His Leu Val Glu Ala Leu Tyr
1               5                  10                  15

Leu Val Cys Gly Glu Arg Gly Phe Phe Xaa Xaa Xaa Xaa Xaa
            20                  25                  30

(2) INFORMATION FOR SEQ ID NO: 3:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO: 3:

Tyr Thr Pro Lys Thr
1               5

(2) INFORMATION FOR SEQ ID NO: 4:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO: 4:

Tyr Thr Pro Lys Ala
1               5

(2) INFORMATION FOR SEQ ID NO: 5:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO: 5:

Ser Asp Asp Ala Arg
1               5

(2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 6:

Glu Glu Ala Glu Ala Glu Ala Glu Pro Lys Ala Thr Arg
1               5                   10

(2) INFORMATION FOR SEQ ID NO: 7:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 7:

Ser Asp Asp Ala Arg
1               5

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 8:

Thr Lys Ser Asp Asp Ala Arg
1               5

(2) INFORMATION FOR SEQ ID NO: 9:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 9:

Lys Ser Asp Asp Ala Arg
1               5

(2) INFORMATION FOR SEQ ID NO: 10:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (xi) SEQUENCE DESCRIPTION: SEQ ID NO: 10:

CCAAGTACAA AGCTTCAACC AAGTGGGAAC CGCACAAGTG TTGGTTAACG AATCTTGTAG      60

CCTTTGGTTC AGCTTCAGCT TCAGCTTCTT CTCTTTTATC CAAAGAAACA CC            112

(2) INFORMATION FOR SEQ ID NO: 11:

(i) SEQUENCE CHARACTERISTICS:

(A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 11:

TAAATCTATA ACTACAAAAA ACACATA                                               27

(2) INFORMATION FOR SEQ ID NO: 12:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO: 12:

TTGGTTGAAG CTTTGTACTT GGTTTGCGGT GAAAGAGGTT TCTTCTACAC TCCTAAGTCT           60

GACGATGCTA GAGGTATTG                                                        79

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 13:

TTAATCTTAG TTTCTAGAGC CTGCGGG                                               27

(2) INFORMATION FOR SEQ ID NO: 14:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 14:

TTGGTTGAAG CTTTGTACTT GGTTTGCGGT GAAAGAGGTT TCTTCTACAC TCCTACCAAG           60

TCTGACGATG CTAGAGGTAT TGTCG                                                 85

(2) INFORMATION FOR SEQ ID NO: 15:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO: 15:

CACTTGGTTG AAGCTTTGTA CTTGGTTTGC GGTGAAAGAG GTTTCTTCTA CACTAAGTCT           60

GACGATGCTA G                                                                71

(2) INFORMATION FOR SEQ ID NO: 16:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO: 16:

CACTTGGTTG AAGCTTTGTA CTTGGTTTGC GGTGAAAGAG GTTTCTTCTA CAAGTCTGAC           60

```
GATGCTAG                                                              68

(2) INFORMATION FOR SEQ ID NO: 17:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO: 17:

CACTTGGTTG AAGCTTTGTA CTTGGTTTGC GGTGAAAGAG GTTTCTTCAA AGTCTGACGA     60

TGCTAG                                                                66

(2) INFORMATION FOR SEQ ID NO: 18:

(i) SEQUENCE CHARACTERISTICS:
        (A) LENGTH: 594 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 109..522

(xi) SEQUENCE DESCRIPTION: SEQ ID NO: 18:

CTTAAATCTA TAACTACAAA AAACACATAC AGGAATTCCA TTCAAGAATA GTTCAAACAA     60

GAAGATTACA AACTATCAAT TTCATACACA ATATAAACGA TTAAAAGA ATG AGA TTT    117
                                                    Met Arg Phe
                                                      1

CCT TCT ATT TTT ACT GCT GTT TTA TTC GCT GCT TCC TCC GCT TTA GCT     165
Pro Ser Ile Phe Thr Ala Val Leu Phe Ala Ala Ser Ser Ala Leu Ala
  5                  10                  15

GCT CCA GTC AAC ACT ACC ACT GAA GAT GAA ACG GCT CAA ATT CCA GCT     213
Ala Pro Val Asn Thr Thr Thr Glu Asp Glu Thr Ala Gln Ile Pro Ala
 20                  25                  30                  35

GAA GCT GTC ATC GGT TAC TCT GAT TTA GAA GGT GAT TTC GAT GTT GCT     261
Glu Ala Val Ile Gly Tyr Ser Asp Leu Glu Gly Asp Phe Asp Val Ala
                 40                  45                  50

GTT TTG CCA TTT TCC AAC TCC ACC AAT AAC GGT TTA TTG TTT ATC AAT     309
Val Leu Pro Phe Ser Asn Ser Thr Asn Asn Gly Leu Leu Phe Ile Asn
             55                  60                  65

ACT ACT ATT GCC TCC ATT GCT GCT AAA GAA GAA GGT GTT TCT TTG GAT     357
Thr Thr Ile Ala Ser Ile Ala Ala Lys Glu Glu Gly Val Ser Leu Asp
         70                  75                  80

AAA AGA TTC GTT AAC CAA CAC TTG TGC GGT TCC CAC TTG GTT GAA GCT     405
Lys Arg Phe Val Asn Gln His Leu Cys Gly Ser His Leu Val Glu Ala
 85                  90                  95

TTG TAC TTG GTT TGC GGT GAA AGA GGT TTC TTC TAC ACT CCT AAG GCT     453
Leu Tyr Leu Val Cys Gly Glu Arg Gly Phe Phe Tyr Thr Pro Lys Ala
100                 105                 110                 115

GCT AAG GGT ATT GTC GAA CAA TGC TGT ACC TCC ATC TGC TCC TTG TAC     501
Ala Lys Gly Ile Val Glu Gln Cys Cys Thr Ser Ile Cys Ser Leu Tyr
                120                 125                 130

CAA TTG GAA AAC TAC TGC AAC TAGACGCAGC CCGCAGGCTC TAGAAACTAA         552
Gln Leu Glu Asn Tyr Cys Asn
                135

GATTAATATA ATTATATAAA AATATTATCT TCTTTTCTTT AT                       594
```

-continued (2) INFORMATION FOR SEQ ID NO: 19:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO: 19:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Phe Val Asn Gln His Leu Cys Gly Ser His Leu
                85                  90                  95

Val Glu Ala Leu Tyr Leu Val Cys Gly Glu Arg Gly Phe Phe Tyr Thr
            100                 105                 110

Pro Lys Ala Ala Lys Gly Ile Val Glu Gln Cys Cys Thr Ser Ile Cys
        115                 120                 125

Ser Leu Tyr Gln Leu Glu Asn Tyr Cys Asn
    130                 135
```

(2) INFORMATION FOR SEQ ID NO: 20:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 20:

```
Thr Gly Gly Lys
1
```

(2) INFORMATION FOR SEQ ID NO: 21:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 21:

```
Thr Glu Gly Lys
1
```

(2) INFORMATION FOR SEQ ID NO: 22:

(i) SEQUENCE CHARACTERISTICS:
        (A) LENGTH: 4 amino acids
        (B) TYPE: amino acid
        (C) STRANDEDNESS: single
        (D) TOPOLOGY: linear

```
        (ii) MOLECULE TYPE: None (xi) SEQUENCE DESCRIPTION: SEQ ID NO: 22:

Gly Asp Thr Lys
1

(2) INFORMATION FOR SEQ ID NO: 23:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 23:

Gly Thr Lys Ser Asp Asp Ala Arg
1               5

(2) INFORMATION FOR SEQ ID NO: 24:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO: 24:

Gly Lys Ser Asp Asp Ala Arg
1               5

(2) INFORMATION FOR SEQ ID NO: 25:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (xi) SEQUENCE DESCRIPTION: SEQ ID NO: 25:

TTGGTTGAAG CTTTGTACTT GGTTTGCGGT GAAAGAGGTT TCTTCTACAC TGGTACCAAG      60

TCTGACGATG CTAGAGGTAT TGTCG                                           85

(2) INFORMATION FOR SEQ ID NO: 26:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 26:

TTGGTTGAAG CTTTGTACTT GGTTTGCGGT GAAAGAGGTT TCTTCTACAC CGGTAAGTCT      60

GACGATGCTA GAGGTATTGT CG                                              82
```